(12) United States Patent
Giancardo et al.

(10) Patent No.: US 10,506,979 B2
(45) Date of Patent: *Dec. 17, 2019

(54) APPARATUS AND METHOD FOR MOTOR FUNCTION CHARACTERIZATION

(71) Applicant: Massachusetts Institute of Technology, Cambridge, MA (US)

(72) Inventors: Luca Giancardo, Houston, TX (US); Alvaro Sanchez Ferro, Cambridge, MA (US); Ian Butterworth, Cambridge, MA (US); Carlos Sanchez Mendoza, Seville (ES)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/834,339

(22) Filed: Dec. 7, 2017

(65) Prior Publication Data

US 2018/0235548 A1    Aug. 23, 2018

Related U.S. Application Data

(63) Continuation of application No. 14/668,945, filed on Mar. 25, 2015, now Pat. No. 9,867,573.

(Continued)

(51) Int. Cl.
*A61B 5/11* (2006.01)
*A61B 5/00* (2006.01)
*A61B 5/1486* (2006.01)

(52) U.S. Cl.
CPC .......... *A61B 5/6897* (2013.01); *A61B 5/1124* (2013.01); *A61B 5/1486* (2013.01);
(Continued)

(58) Field of Classification Search
CPC ... A61B 5/6897; A61B 5/1124; A61B 5/7278; A61B 5/7246; A61B 5/7267;
(Continued)

(56) References Cited

U.S. PATENT DOCUMENTS 8,233,613 B1 * 7/2012 Michaelis ........... H04M 1/2474
  379/422
8,285,658 B1   10/2012 Kellas-Dicks et al.
(Continued)

FOREIGN PATENT DOCUMENTS

WO    WO 2007/078756 A2    7/2007
WO    WO 2012/128952 A2    9/2012

OTHER PUBLICATIONS

US 8,621,363 B2, 12/2013, Bromer (withdrawn)
(Continued)

*Primary Examiner* — An T Nguyen
(74) *Attorney, Agent, or Firm* — Wolf, Greenfield & Sacks, P.C.

(57) ABSTRACT

Analysis of keystroke dynamics performed by an individual can be used for assessment and monitoring of the individual's motor function. Keystroke events related to a user pressing one or more keys on a keyboard or regions on a touch screen may be analyzed to identify a plurality of distributions of keystroke event intervals. The plurality of distributions may be analyzed to identify one or more features indicative of variation among the distributions and indicative of the user's motor function. Monitoring of a user's motor function may include comparing a value for a feature for one plurality of distribution to a second value for the same feature for another plurality of distributions.

19 Claims, 13 Drawing Sheets

Related U.S. Application Data

(60) Provisional application No. 61/969,940, filed on Mar. 25, 2014.

(52) U.S. Cl.
CPC .......... *A61B 5/4082* (2013.01); *A61B 5/7246* (2013.01); *A61B 5/7267* (2013.01); *A61B 5/7278* (2013.01); *A61B 5/7282* (2013.01); *A61B 5/1101* (2013.01)

(58) Field of Classification Search
CPC ... A61B 5/7282; A61B 5/0022; A61B 5/4806; A61B 5/486; A61B 5/4088; A61B 5/6898
See application file for complete search history.

(56) References Cited

U.S. PATENT DOCUMENTS

| | | |
|---|---|---|
| 8,346,680 B2 | 1/2013 | Castleman et al. |
| 8,671,347 B2 | 3/2014 | Bromer |
| 9,867,573 B2 | 1/2018 | Giancardo et al. |
| 2005/0065452 A1 | 3/2005 | Thompson |
| 2006/0189885 A1* | 8/2006 | Yelland .................. A61B 5/16 600/558 |
| 2006/0195328 A1 | 8/2006 | Abraham et al. |
| 2008/0091639 A1 | 4/2008 | Davis et al. |
| 2008/0092209 A1 | 4/2008 | Davis et al. |
| 2008/0098456 A1 | 4/2008 | Alward et al. |
| 2009/0002178 A1 | 1/2009 | Guday et al. |
| 2009/0018407 A1 | 1/2009 | Jung et al. |
| 2009/0024332 A1 | 1/2009 | Karlov et al. |
| 2012/0021391 A1 | 1/2012 | Elsmore et al. |
| 2012/0098750 A1* | 4/2012 | Allen ..................... G06F 3/023 345/169 |
| 2012/0235819 A1 | 9/2012 | Watkins et al. |
| 2013/0176413 A1 | 7/2013 | Lowry et al. |
| 2014/0074267 A1 | 3/2014 | Alberts et al. |
| 2014/0114889 A1* | 4/2014 | Dagum ............... G06F 19/3418 706/12 |
| 2014/0121559 A1* | 5/2014 | Stevens .................. A61B 5/16 600/558 |
| 2015/0272504 A1 | 10/2015 | Giancardo et al. |

OTHER PUBLICATIONS

Banerjee et al., Biometric Authentication and Identification using Keystroke Dynamics: A Survey. J. Pattern Rec Res. 2012;7:116-139.

Bronte-Stewart et al., Quantitative digitography (QDG): a sensitive measure of digital motor control in idiopathic Parkinson's disease. Mov Disord. Jan. 2000;15(1):36-47.

Epp et al., Identifying emotional states using keystroke dynamics. Proceedings of the SIGCHI Conference on Human Factors in Computing Systems. May 7-12, 2011. 715-724.

Jain et al., Biometrics of Next Generation: An Overview. 2010.

Killourhy et al., Comparing anomaly-detection algorithms for keystroke dynamics. Dependable Systems & Networks, 2009. IEEE/IFIP International Conference. 125-134.

Killourhy, A Scientific Understanding of Keystroke Dynamics. Jan. 2012. Thesis. Carnegie Mellon University.

Memedi et al., Automatic and objective assessment of alternating tapping performance in Parkinson's disease. Sensors (Basel). Dec. 9, 2013;13(12):16965-84. doi: 10.3390/s131216965.

Okuno et al., Finger taps movement acceleration measurement system for quantitative diagnosis of Parkinson's disease. Conf Proc IEEE Eng Med Biol Soc. 2006;Suppl:6623-6.

Vizer et al., Detecting cognitive and physical stress through typing behavior. SIG CHI EA Apr. 4-9, 2009. 3113-3116.

Vizer et al., Detecting Cognitive Impairment Using Keystroke and Linguistic Features of Typed Text: Toward an Adaptive Method for Continuous Monitoring of Cognitive Status. Lecture Notes Comp Sci. 2011;7058:483-500.

Wall et al., Can Motor Measures Tell Us If Someone Is Trying? An Assessment of Sincerity of Effort in Simulated Malingering. Int. J. Rehab Health. 1998;4(1):51-57.

PCT/US2015/022581, Jun. 12, 21015, Invitation to Pay Additional Fees.

PCT/US2015/022581, Aug. 13, 2015, International Search Report and Written Opinion.

PCT/US2015/022581, Oct. 6, 2016, International Preliminary Report on Patentability.

EP 15770079.0, Feb. 5, 2018, Extended European Search Report.

\* cited by examiner

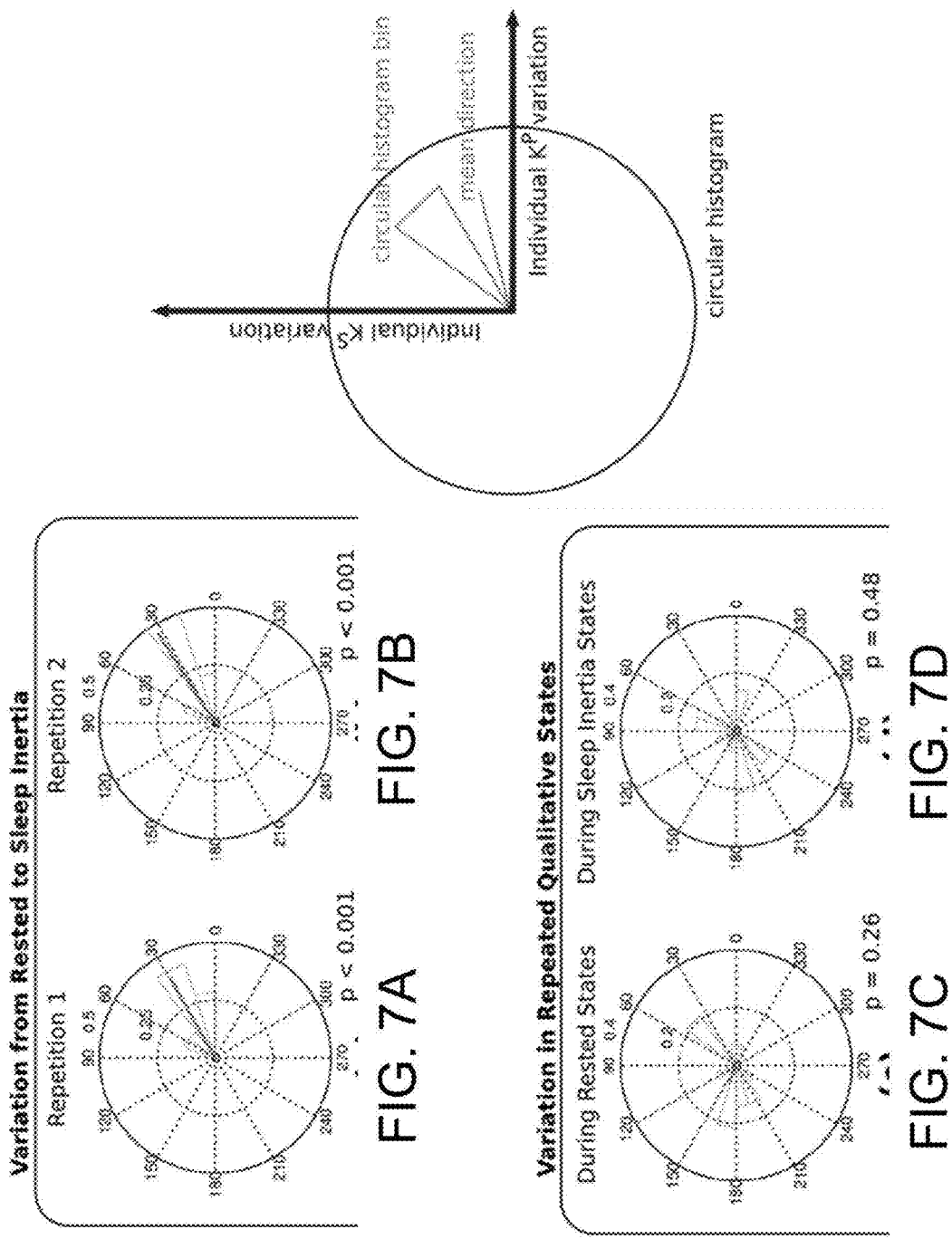

APPARATUS AND METHOD FOR MOTOR FUNCTION CHARACTERIZATION

RELATED APPLICATIONS

This application is a continuation of and claims the benefit under 35 U.S.C. § 120 of U.S. application Ser. No. 14/668,945 filed on Mar. 25, 2015 and titled "APPARATUS AND METHOD FOR MOTOR FUNCTION CHARACTERIZATION," which is hereby incorporated herein by reference in its entirety. Application Ser. No. 14/668,945 claims priority under 35 U.S.C. § 119(e) to U.S. Provisional Application Ser. No 61/969,940, filed on Mar. 25, 2014, which is herein incorporated by reference in its entirety.

BACKGROUND

Neurological disease and motor impairment underlie many diseases and conditions. The causes and manifestations of these conditions and diseases are diverse and numerous. Examples of causes of psychomotor impairment are: onset of neurological illnesses (such as Alzheimer, Parkinson's disease, traumatic brain injuries, attention deficit disorders), motor illnesses (such as osteoarthritis), psychiatric conditions (such as depression, anxiety, psychosis, personality disorders), developmental disorders, age, licit and illicit drugs (alcohol included), fatigue, stress, sleepiness, dehydration. There currently is not a single mechanism for detecting and characterizing motor impairment arising from different sources.

SUMMARY

One type of embodiment is directed to a method of characterizing motor function of a user by analyzing an input by the user to a user interface of at least one computing device. The method comprises receiving a sequence of keystroke events indicating that the user pressed at least a portion of the user interface over a time duration, determining, by at least one processor, a plurality of distributions of keystroke event intervals over at least some of the time duration, wherein each distribution of the plurality of keystroke distributions corresponds to a portion of the time duration, the plurality of distributions of keystroke event intervals comprises a first distribution relating to keystroke events included in a first portion of the time duration and a second distribution relating to keystroke events included in a second portion of the time duration, wherein determining a distribution of the plurality of distributions comprises identifying time intervals between keystroke events that occur within a corresponding portion of the time duration, and determining a stability of the motor function of the user at least in part by analyzing at least the first distribution and the second distribution to determine variation of keystroke event intervals over the time duration.

In some embodiments, receiving the sequence of keystroke events comprises receiving a sequence of a plurality of key selection events, and identifying time intervals between keystroke events comprises identifying time intervals between key selection events of the plurality of key selection events. In some embodiments, determining a stability of the motor function of the user comprises analyzing at least the first distribution and the second distribution to determine a measure of variation in width of at least the first distribution and the second distribution. In some embodiments, analyzing at least the first distribution and the second distribution comprises: calculating at least one feature of the first and second distributions and determining variation of the at least one feature between the first and second distributions. In some embodiments, calculating the at least one feature comprises calculating a median keystroke event interval for each distribution of the plurality of distributions and analyzing at least the first and second distributions comprises calculating an average median keystroke event interval by averaging the median keystroke event intervals for each distribution. In some embodiments, calculating the at least one feature comprises comparing at least the first distribution to the second distribution to obtain a degree of similarity indicative of the variation among the plurality of distributions. In some embodiments, calculating the at least one feature comprises comparing each distribution of the plurality of distributions to each distribution of the plurality of distributions to obtain a degree of similarity indicative of the variation among on the plurality of distributions.

In some embodiments, determining a distribution of the plurality of distributions comprises identifying a plurality of keystroke time intervals between keystroke events related to the user pressing a key of the user interface. In some embodiments, determining a distribution of the plurality of distributions comprises identifying a plurality of keystroke time intervals between keystroke events related to the user pressing a key of the user interface and a subsequent key of the user interface. In some embodiments, determining a distribution of the plurality of distributions comprises identifying a plurality of keystroke time intervals between keystroke events related to the user pressing a first key of the plurality of keys and a second key of the plurality of keys before releasing the first key. In some embodiments, the first portion of the time duration and the second portion of the time duration are non-overlapping portions of the time duration.

In some embodiments, receiving the sequence of keystroke events comprises receiving a sequence of keystroke events input by the user while interacting with a plurality of different applications executing on the at least one computing device. In some embodiments, receiving the sequence of keystroke events comprises receiving a sequence of keystroke events input by the user with a plurality of processes executing on the at least one computing device.

In some embodiments, the method further comprises receiving a second sequence of keystroke events indicating that the user pressed at least a portion of the user interface over a second time duration, determining, by the at least one processor, a second plurality of distributions of keystroke event intervals over at least some of a second time duration, wherein each distribution of the second plurality of keystroke distributions corresponds to a portion of the second time duration, the second plurality of distributions of keystroke event intervals comprises a third distribution relating to keystroke events included in a first portion of the second time duration and a fourth distribution relating to keystroke events included in a second portion of the second time duration, wherein determining a second distribution of the plurality of distributions comprises identifying time intervals between keystroke events that occur within a corresponding portion of the second time duration, and determining a second stability of the motor function of the user at least in part by analyzing at least the third distribution and the fourth distribution to determine variation of keystroke event intervals over the second time duration.

In some embodiments, the method further comprises identifying a change, if any, in the user's motor functions between the time duration and the second time duration by comparing the plurality of distributions to the second plurality of distributions. In some embodiments, a difference between the time duration and the second time duration is a time period over days. In some embodiments, a difference between the time duration and the second time duration is a time period over months. In some embodiments, a difference between the time duration and the second time duration is a time period over years.

In some embodiments, identifying a change in the user's motor functions between the time duration and the second time duration comprises determining a first feature related to variation in distribution spread among the plurality of distributions and a second feature related to variation in distribution spread among the second plurality of distributions and comparing at least the first feature and the second feature. In some embodiments, identifying a change in the user's motor functions between the time duration and the second time duration comprises determining a difference between at least the first feature and at least the second feature. In some embodiments, identifying a change in motor function between the time duration and the second time duration comprises identifying a measure of an increase in hold time when the user presses a key based on comparing the plurality of distributions and the second plurality of distributions. In some embodiments, the identified change in the user's motor function indicates that the user's motor function is impaired.

In some embodiments, the method further comprises determining an average value for the plurality of distributions by averaging a plurality of median values, wherein each median value is a median keystroke event interval for a distribution of the plurality of distributions, determining a second average value for the second plurality of distributions by averaging a plurality of median values, wherein each median value is a median keystroke event interval for a distribution of the second plurality of distributions, determining a degree of similarity indicative of a variation among the plurality of distributions for the plurality of distributions by comparing the plurality of distributions to each other, determining a second degree of similarity indicative of a variation among the plurality of distributions for the second plurality of distributions by comparing the second plurality of distributions to each other, identifying a feature vector based on the average value and the degree of similarity, and identifying a second feature vector based on the second average value and the second degree of similarity, wherein identifying a change in the user's motor functions between the time duration and the second time duration comprises determining a difference between the feature vector and the second feature vector.

In some embodiments, the method further comprises determining a first quantile and a second quantile for a distribution of the plurality of distributions, identifying key stroke event intervals in the distribution as outliers based on the first quantile, calculating a number of outliers in the distribution based on the identified at least one outlier, normalizing the number of outliers by a number of key presses for the distribution, calculating a difference between the first quantile and the second quantile, calculating a standard deviation of the outliers, calculating a value based on at least a portion of a covariance of the plurality of distributions, and determining a feature vector based on the number of outliers, the difference, the standard deviation, and the value.

In some embodiments, the method further comprises determining, via a machine learning classifier, a second feature vector based a second distribution of the plurality of distributions. In some embodiments, the user interface is a physical keyboard or a virtual keyboard.

In some embodiments, the method further comprises presenting, via a second user interface, a report providing a characterization of the user's motor functions as a condition based on the stability of the user's motor function.

In some embodiments, the method further comprises determining a feature from information related to measurements performed by sensor in communication with the computing device.

Another type of embodiment is directed to at least one computer-readable storage medium storing computer-executable instructions that, when executed, perform a method of characterizing motor function of a user by analyzing an input by the user to a user interface of at least one computing device. The method comprises receiving a sequence of keystroke events indicating that the user pressed at least a portion of the user interface over a time duration, determining, by at least one processor, a plurality of distributions of keystroke event intervals over at least some of the time duration, wherein each distribution of the plurality of keystroke distributions corresponds to a portion of the time duration, the plurality of distributions of keystroke event intervals comprises a first distribution relating to keystroke events included in a first portion of the time duration and a second distribution relating to keystroke events included in a second portion of the time duration, wherein determining a distribution of the plurality of distributions comprises identifying time intervals between keystroke events that occur within a corresponding portion of the time duration, and determining a stability of the motor function of the user at least in part by analyzing at least the first distribution and the second distribution to determine variation of keystroke event intervals over the time duration.

Another type of embodiment is directed to a system for characterizing motor function of a user by analyzing an input by the user to a user interface of at least one computing device. The system comprises at least one processor configured to receive a sequence of keystroke events indicating that the user pressed at least a portion of the user interface over a time duration and at least one storage medium storing processor-executable instructions that, when executed by the at least one processor, perform a method comprising: determining a plurality of distributions of keystroke event intervals over at least some of the time duration, wherein each distribution of the plurality of keystroke distributions corresponds to a portion of the time duration, the plurality of distributions of keystroke event intervals comprises a first distribution relating to keystroke events included in a first portion of the time duration and a second distribution relating to keystroke events included in a second portion of the time duration, wherein determining a distribution of the plurality of distributions comprises identifying time intervals between keystroke events that occur within a corresponding portion of the time duration, and determining a stability of the motor function of the user at least in part by analyzing at least the first distribution and the second distribution to determine variation of keystroke event intervals over the time duration.

Another type of embodiment is directed to a method of characterizing motor function of a user by analyzing an input by the user to a user interface of at least one computing device. The method comprises receiving a sequence of keystroke events indicating that the user pressed at least a portion of the user interface over a time duration while the user is interacting with a plurality of different applications executing on the at least one computing device, determining, by at least one processor, a plurality of distributions of keystroke event intervals over at least some of the time duration, wherein each distribution of the plurality of keystroke distributions corresponds to a portion of the time duration and determining a distribution of the plurality of distributions comprises identifying time intervals between keystroke events that occur within a corresponding portion of the time duration, and determining a stability of the motor function of the user at least in part by analyzing at least the first distribution and the second distribution to determine variation of keystroke event intervals over the time duration.

Another type of embodiment is directed to a method of characterizing motor function of a user by analyzing an input by the user to a user interface of at least one computing device. The method comprises receiving a sequence of keystroke events indicating that the user pressed at least a portion of the user interface over a time duration with a plurality of processes executing on the at least one computing device, determining, by at least one processor, a plurality of distributions of keystroke event intervals over at least some of the time duration, wherein each distribution of the plurality of keystroke distributions corresponds to a portion of the time duration and determining a distribution of the plurality of distributions comprises identifying time intervals between keystroke events that occur within a corresponding portion of the time duration, and determining a stability of the motor function of the user at least in part by analyzing at least the first distribution and the second distribution to determine variation of keystroke event intervals over the time duration.

Another type of embodiment is directed to an apparatus comprising a user interface and control circuitry configured to perform a method comprising: receiving a sequence of keystroke events indicating that the user pressed at least a portion of the user interface over a time duration; determining a plurality of biosignatures indicative of the user's motor function at different times by determining, for a biosignature of the plurality of biosignatures, a plurality of distributions of keystroke event intervals over at least some of the time duration, wherein each distribution of the plurality of keystroke distributions corresponds to a portion of the time duration; and monitoring motor function in the user by tracking a condition of the user's motor function over time based on comparing a first biosignature of the plurality of biosignatures with a second biosignature.

In some embodiments, comparing the first biosignature of the plurality of biosignatures with the second biosignature comprises identifying a first stability level for the first biosignature and a second stability level for the second biosignature and determining a difference between the first stability level and the second stability level. In some embodiments, determining the difference between the first stability level and the second stability level indicates a decrease in stability and the tracked condition indicates impairment of the user's motor function over time. In some embodiments, the control circuitry is further configured to issue a report related to the tracked condition to the user. In some embodiments, the control circuitry is further configured to issue a report related to the tracked condition to a medical provider. In some embodiments, the second biosignature is a biosignature of the plurality of biosignatures corresponding to an earlier time than the first biosignature. In some embodiments, the second biosignature is associated with a second user having motor function that is identified as being unimpaired.

In some embodiments, the user interface is a user interface of a first computing device, the control circuitry is a component of at least one second computing device different from the first computing device, and the first computing device and the at least one second computing device are adapted to communicate over at least one network.

Another type of embodiment is directed to a method of characterizing motor function of a user by analyzing an input by the user to a user interface of at least one computing device. The method comprises receiving a sequence of keystroke events indicating that the user pressed at least a portion of the user interface over a time duration, determining a plurality of biosignatures indicative of the user's motor function at different times by determining, for a biosignature of the plurality of biosignatures, a plurality of distributions of keystroke event intervals over at least some of the time duration, wherein each distribution of the plurality of keystroke distributions corresponds to a portion of the time duration, and monitoring motor function in the user by tracking a condition of the user's motor function over time based on comparing a first biosignature of the plurality of biosignatures with a second biosignature.

In some embodiments, the method further comprises identifying impairment in the user's motor function over time based on monitoring the user's motor function and comparing a characterization of the user's motor function to characterizations of motor function associated with a plurality of conditions and, when the characterization of the user's motor function matches a characterization associated with a condition, storing an indication that the user may have the condition.

In some embodiments, the method further comprises outputting a message containing an indication that the user may have impaired motor function. In some embodiments, the method further comprises outputting a message indicating that the user may have a neurological disorder. In some embodiments, the method further comprises outputting a message indicating that the user may have a condition of sleep deprivation. In some embodiments, outputting a message indicating that the user may have a condition of intoxication. In some embodiments, the method further comprises outputting a message indicating that the user may have a cognitive impairment. In some embodiments, the method further comprises outputting a message indicating that the user may have a condition of arthritis. In some embodiments, the method further comprises outputting a message indicating that the user may have a condition of sleep inertia.

Another type of embodiment is directed to a method for characterizing a psychomotor impairment in a user. The method comprises detecting a plurality of keystroke events as a background task while the user is interacting with a device sensitive to touch, determining time intervals associated with the keystroke events, and characterizing a psychomotor impairment in the user based on the time intervals associated with the keystroke events.

Another type of embodiment is directed to a method for early detection of a neurological disease in a user. The method comprises detecting a plurality of keystroke events while the user is interacting with a device sensitive to touch, determining time intervals associated with the keystroke events, and identifying the presence of a neurological disease in the user prior to diagnosis of physical symptoms in the user.

Another type of embodiment is directed to an electronic device comprising a tactile interface for receiving a plurality of keystrokes, a processor configured to receive user input from the tactile interface on the plurality of keystrokes, and a storage medium storing processor executable instructions that when executed by the processor perform a method comprising determining a plurality of distributions of keystroke event intervals over at least some of the time duration, wherein each distribution of the plurality of keystroke distributions corresponds to a portion of the time duration, the plurality of distributions of keystroke event intervals comprises a first distribution relating to keystroke events included in a first portion of the time duration and a second distribution relating to keystroke events included in a second portion of the time duration, wherein determining a distribution of the plurality of distributions comprises identifying time intervals between keystroke events that occur within a corresponding portion of the time duration; and analyzing at least the first distribution and the second distribution to determine variation of keystroke event intervals over the time duration.

In some embodiments, the electronic device is a computer. In some embodiments, the electronic device is a tablet. In some embodiments, the electronic device is a touch screen.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 7A-D are circular histograms illustrating differences in a feature vector for two different pluralities of distributions corresponding to individuals in rested and sleep inertia states.

DETAILED DESCRIPTION

Figure 1:
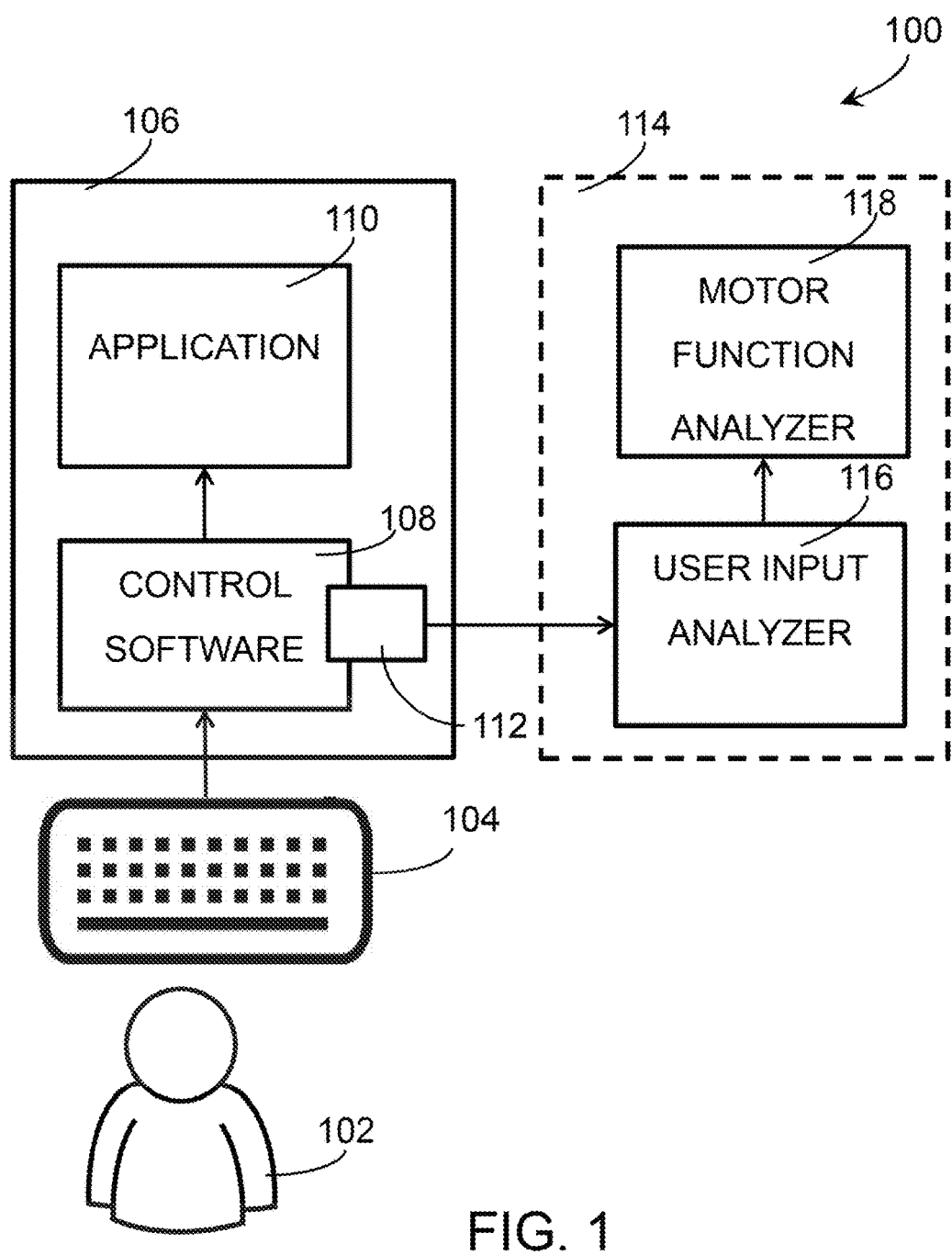
FIG. 1 is a schematic of an exemplary system that performs characterization of a user's motor function.

The inventors have recognized and appreciated that operating a diagnostic tool to produce biosignatures indicative of a person's motor function, such as by analyzing keystroke events to determine a distribution of keystroke event intervals, may provide an improved mechanism for evaluating that person's motor function and aiding in the diagnosis of neurological impairments. Such a diagnostic tool may evaluate a motor function of a person through analyzing a sequence of keystroke events indicating keyboard keys, such as physical or touchscreen keyboard keys, that the person has pressed over a period of time. A keystroke event, as used herein, refers to the act of employing fingers on a mechanical input device (such as buttons) or surfaces able to detect such interaction (such as touchscreens). In some particularly advantageous embodiments, the sequence of keystroke events may be collected while the person interacts with multiple different applications executing on a computing device, such as while the person is using a computing device to perform tasks unrelated to diagnosing motor function impairment.

A person's "motor function" relates to the ways in which the person's muscles move or ways in which a person's muscles move the person's limbs or digits. Motor function may indicate a health of a person or, conversely, a variety of conditions that may exist in the person, including neurological disorders (e.g., Parkinson's Disease, Parkinsonism, Amyotrophic Lateral Sclerosis, forms of Dementia such as Alzheimer's Disease and Mild Cognitive impairment) the person may be suffering from or other neurological impairments such as brain injury (e.g., concussions), motor illnesses such as osteoarthritis, psychiatric conditions such as personality disorders, depression, anxiety, psychosis, developmental disorders, transient conditions such as intoxication, fatigue, stress, and dehydration. Monitoring of a person's motor function may therefore aid in diagnosing conditions that may result in impaired motor function of the person.

The inventors have therefore recognized and appreciated that, by measuring a person's motor function, the person's neurological status can be assessed and/or diagnosed. For example, at a given time, the person's motor function may be compared to a previous indication of motor function obtained at an earlier time to achieve a degree of motor function impairment. Additionally or alternatively, the person's motor function may be compared to a reference person's motor function, such as a person who has been identified as unimpaired, to determine a degree of motor function impairment. In this manner, monitoring of a person's motor function and the person's condition related to the person's motor function may be performed over time as part of assessing and/or diagnosing conditions such as neurological conditions, arthritis, sleep deprivation, and/or intoxication.

The inventors have recognized and appreciated that it would be particularly advantageous if diagnostic tools were able to identify changes in motor function early, which would in turn allow for early screening of motor-comprised conditions including neurodegenerative conditions, psychological disorders, and/or transient conditions such as intoxication.

The inventors have additionally recognized and appreciated that a person's keystrokes while typing on a keyboard may provide an indication of the person's motor function. The term keystroke and keyboard are used throughout the application to refer to the physical depressing of keys such as on a physical keyboard as well as the touch of a touch screen. More particularly, the inventors have recognized and appreciated that the dynamics associated with a person's keystrokes may be indicative of motor function. As a person performs a typing task, that person will press and release individual keys of a keyboard or regions of a touch screen that relate to letters, numbers or other functionalities. Analysis of the timing associated with the pressing and releasing of individual keys or regions of a screen may provide an indication of the person's motor function. For example, specific time variables associated with keystroke dynamics, including hold time, press latency, flight time, and/or release latency, may be influenced by a person's motor function and thus may, once analyzed, provide an indication of that person's motor function. In this manner, a person's user input for one or more processing tasks may be analyzed to determine characteristics of the person's keystroke dynamics, and to assess the person's motor function.

The inventors have therefore recognized the advantages of a diagnostic tool that analyzes keystroke events collected during a person's operation of a computing device to derive time variables associated with keystroke dynamics and that analyzes the time variables to assess a person's motor function. By monitoring the person's user input over time using such a tool, changes in the time intervals may be tracked and assessed to determine potential changes in motor function over time. The diagnostic tool may analyze the time intervals by generating distributions of keystroke timing information in time intervals, and by compiling such distributions of timing intervals to form biosignatures that are indicative of a person's motor function. Analyzing the timing information set forth within one biosignature, and/or comparing biosignatures, may enable motor function to be reliably assessed.

Moreover, the inventors have recognized and appreciated that such data on keystroke events may be collected while individuals are interacting with their personal computing devices, such as personal computers, mobile phones, tablet computers, or personal digital assistants while they perform routine tasks unrelated to diagnosis. Because individuals interact often with electronic devices in ways that require user input to be provided through keystroke events, a diagnostic tool that monitors a person's keystroke dynamics while the person interacts with personal computing device(s) may have a lower burden on users and enable more frequent and consistent monitoring of the person's motor function than though scheduled visits to a facility designated to evaluate motor function, such as a medical facility. This may permit more data to be captured and analyzed over time. Accordingly, characterization of motor function according to techniques described herein may provide an earlier indication of motor function impairment, such as before the onset of symptoms indicating a higher level of impairment in motor function (e.g., tremors or stiffness in people with Parkinson's disease), than is available with other diagnostic tools. This may in turn allow for earlier intervention for treatment of the causes of any neurological impairment.

Other electronic devices may have physical and/or virtual keys that may collect data on keystroke events such as remote controllers, household appliances (e.g., refrigerators, coffee machines, microwaves), industrial machines and appliances, medical electronic devices, and motor vehicle panels (e.g., entertainments system, control panels, Global Positioning Systems). Keystroke events collected from a device may be used to monitor motor function of a person while the person is performing a task and/or operating the device without altering the functionality of the device. As an example, a control panel of a motor vehicle may collect keystroke events related to input from a driver of the motor vehicle which may be analyzed to provide an indication of motor function impairment due to a condition such as a state of fatigue or sleep deprivation. This may allow for an intervention to deter the driver from operating the motor vehicle.

Accordingly, described herein are embodiments of a diagnostic tool for aiding in evaluating motor function of a person by analyzing keystroke events resulting from input by a person to a keyboard, such as a physical keyboard or a touchscreen keyboard. In some embodiments, the analysis performed by the diagnostic tool may include identifying time information associated with keystroke events related to a user input and identifying keystroke event intervals, such as hold time and press latency, from the time information. The tool may also calculate distributions (e.g., histograms or probability density functions) of keystroke event intervals over portions of time, which may assist in identifying variations in the keystroke event intervals. By analyzing different features of the distributions, variation among the distributions may be determined and provide an indication of the user's motor function.

Lack of variation or narrow variation among distributions may indicate stability in the user's motor function, while broad variation among the distributions may indicate instability of the user's motor function. Variation among different distributions may be identified by changing peak values and/or spread of the distributions. As an example, distributions of times associated with a user pressing keys or a region of a screen or "hold time" may be determined and variation among the distributions may indicate a stability of the user's motor function. In some embodiments, the distributions may be compared with each other to identify a level of similarity among the distributions indicative of stability of the user's motor function. A set of distributions acquired over a time duration may provide a biosignature for a person throughout the time duration.

In some embodiments, the analysis performed by the diagnostic tool may include comparing different sets of distributions acquired at different time durations to identify changes in stability of the user's motor function. In some embodiments, an average of peak values from one set of distributions may be compared with an average of peak values from another set of distributions. For example, an average value for hold time may be compared between two different sets of distributions. The two sets of distributions may be determined for time durations separated by days, months, or years. An increase in average hold time may indicate impairment in the person's motor function, while no or little change in average hold time may indicate stability in the person's motor function.

In some embodiments, one or more sensors may provide additional data used to detect other aspects relevant to a user's motor function. A sensor may be a built-in sensor integrated as part of an electronic device or a separate component in communication with an electronic device. Measurements performed by one or more sensors of the electronic device may provide additional information that may be complementary to the information acquired through analysis of keystroke events. A sensor may measure motion, orientation, position, typing pressure, and/or various environmental conditions. A sensor may be an accelerometer, gravity sensor, gyroscope, rotational vector sensor, orientation sensor, a magnetometer, pressure sensor, thermometer, barometer, microphone, and/or photometer. A diagnostic tool may analyze data from one or more sensors (e.g. accelerometer data, gyroscope data, typing pressure data, location data, voice data). In some embodiments, the analysis performed by the diagnostic tool may include analyzing information from one or more sensors that is associated with keystroke events related to a user input.

Examples of diagnostic tools operating in accordance with techniques explained above are described below, but it should be appreciated that the examples are provided merely for purposes of illustration and that other implementations are possible.

FIG. 1 illustrates an exemplary embodiment of a system 100 for assessing a user's motor function. The system 100 includes user interface 104 that is a component of and/or in communication with computing device 106. Using techniques described herein, the system 100 may analyze a user's interactions with keys or screen regions of the user interface 104.

As shown in the example of FIG. 1, user interface 104 may include a physical keyboard having a plurality of physical keys. As an example, in cases in which device 106 is a typical laptop or desktop personal computer, interface 104 may include a full-size physical keyboard having keys organized in a typewriter layout (a "QWERTY" layout) or other key arrangement. Such a keyboard may be, for example, an external keyboard as an added component that connects to other components of the computing device 106 via a wired and/or wireless connection. In other cases, device 106 is implemented as another computing device, such as a mobile telephone, handheld computer or smartphone, and the interface 104 may instead include a miniature keyboard integrated as part of the computing device 106. As is known, a keyboard is typically operated by a user's hands/fingers. User 102 would use his or her fingers to activate individual keys of the keyboard by touching and/or pressing them.

While a physical keyboard is illustrated in FIG. 1, it should be appreciated that embodiments are not limited to operating with a particular type of keyboard or keys. In some embodiments, the user interface 104 may include a touchscreen instead or in addition to a physical keyboard. A touchscreen includes a visual display on which a program executing on the computing device 106 can present information. A user can provide input by touching the screen, typically with the user's fingers or a stylus. The touchscreen responds to the input by providing an indication of where the screen was touched. Software of the interface 104 and/or control software 108 of the computing device 106 may correlate the indication of where the user touched the touch screen to what information was being displayed at that time. Depending on the nature of the contact with the touch screen and/or the information displayed on the touch screen at the location of that contact, the output of the touch screen may be interpreted differently. The touch screen, for example, may be configured with graphics representing keys. When the user contacts the touch screen at a location occupied by a display of a key, the electronic device may respond just like it would to a user input through a keyboard designating the same key. A computer configured in this way may be said to have a virtual keyboard. When there is a virtual keyboard on the screen, a user may select a key on the keyboard by touching the location of the key on the screen. An application may interpret the touched location as keyboard input information, indicating that output information associated with the key is to be displayed, such as text characters like "B" or "L". Additionally, a user may touch a location on the screen to select a link, such as to open an application or link. The operating system may interpret the touched location as navigational information, indicating that output information associated with touching the particular location is to be displayed.

Regardless of the type of user interface, interface 104 may generate information indicating interactions of the user with the interface 104. That indication may be passed from interface 104 to control software 108, which may be implemented as part of an operating system, firmware, or other suitable control software for interacting with device hardware. Control software 108 may then pass the indication of the input to application program 110 executing on computing device 106. In this manner, user 102 may provide input while an application or process 110 is executing on computing device 106, which may be input that the user 102 provides to the application or process 110.

In some embodiments in which the keystroke events are user input to an application or process 110, the application or process 110 may be a diagnosis application that requests that user 102 provide input in the form of keystrokes for the purpose of testing motor function. In other embodiments that may be particularly advantageous in some scenarios, the application or process 110 may be unrelated to medical testing and diagnosis, including unrelated to testing motor function. In such cases, the application or process 110 may be related to performing one or more processing tasks on computing device 106 that are personal or professional tasks for the user 102, such as internet browsing, document editing or other word processing, data entry, or other applications. In some such embodiments, the application or process 110 may be multiple different applications/processes that are unrelated to medical testing or diagnosis. In such cases, collection and/or analysis of user input may be performed as a background process, while the application(s) or process(es) 110 is/are executing on computing device 106.

In accordance with techniques described herein, in addition to being passed to the application/process 110, information regarding interactions of a user with the interface 104 may be passed to a motor function characterization system 114. In some embodiments, control software 108 may pass the information on the interactions with the interface 104 to the system 114. In other embodiments, a module 112 may collect the information on the user input from the control software 108 and/or application 110 and occasionally, periodically, or continuously (e.g., as the information is received) transmit the information on the user input to the system 114. In some embodiments, module 112 may collect information on measurement data from one or more sensors integrated in computing device 106 or in communication with computing device 106. In some embodiments, the one or more sensors may be integrated in user interface 104. As an example, pressure sensors as part of a touchscreen may measure pressure as a user touches a location of the touchscreen such as a virtual key. The one or more sensors may provide information related to the user's movement, location, orientation, voice, and/or typing pressure. Module 112 may occasionally, periodically, or continuously (e.g., as the information is received) transmit information from the one or more sensors to system 114. In some embodiments, the module 112 may be a component of the control software 108 (e.g., a component of an operating system) or a component of the application 110, such as a plug-in to the application 110. Embodiments are not limited to implementing the module 112 in any particular manner.

In the example of FIG. 1, motor function characterization system 114 includes user input analyzer 116 and motor function analyzer 118. The user input analyzer 116 receives data regarding a user input from the device 106. In some embodiments, user input analyzer 116 may receive that data in the form of a sequence of keystroke events. A keystroke event may include information relating to a user pressing or releasing a key. A sequence of keystroke events may include only press events, only release events, or both. Keystroke events of the sequence may be formatted as operating system events or events output by a device driver, and/or may be implemented in another format containing other information. As such, in embodiments in which the control software 108 is implemented as an operating system, the keystroke events may be provided as an output from operating system 108 and indicate that the user pressed one or more keys or otherwise operated a touchscreen.

In some embodiments, the sequence of keystroke events may include a sequence of multiple key selection events. A key selection event may be associated with a user pressing keys on a keyboard, such as physical or touchscreen keyboard. The "key down" event may be associated with a user depressing a physical key of a physical keyboard or initiating contact with a touchscreen. A "key up" event may be associated with a user releasing a physical key of a physical keyboard or ending contact with a touchscreen.

The sequence of keystroke events received by the user input analyzer 116 may indicate that the user pressed one or more keys or touches over a time duration, and may include time information for each of the keystroke events. The user input analyzer 116 may analyze the keystroke event information, including the time information, from the sequence as part of analyzing a user's motor function, as described in detail below.

Results of keystroke event analysis produced by the user input analyzer 116 may be provided to a motor function analyzer 118. Motor function analyzer 118 may analyze the information provided by the user input analyzer 116 and produce information indicative of a motor function of the user 102, which may include one or more biosignatures for the user 102 and/or one or more distributions of time intervals for keystroke events. From analyzing the biosignature(s) and/or distribution(s), the motor function analyzer 118 may generate information on whether the user 102 appears to have a healthy motor function or whether the user 102 appears to have an impaired motor function. The motor function analyzer 118 may also, in some embodiments, be configured to produce indications of one or more conditions that analysis of the sequence of keystroke events indicates the user 102 may have, which the analyzer 118 may output for review by the user 102 and/or a clinician who may diagnose the user 102.

Motor function characterization system 114 may be implemented in any suitable form. While motor function characterization system 114 is illustrated in FIG. 1 as separate from the computing device 106, it should be appreciated that one or more components of motor function characterization system 114 may be part of computing device 106 and/or part of one or more other computing devices. In some embodiments, for example, motor function characterization system 114 may be implemented as a single stand-alone machine, or may be implemented by multiple distributed machines that share processing tasks in any suitable manner, that is/are separate from the computing device 106 operated by the user 102. Motor function characterization system 114 may be implemented as one or more computers; an example of a suitable computer is described below. In some embodiments, motor function characterization system 114 may include one or more tangible, non-transitory computer-readable storage devices storing processor-executable instructions, and one or more processors that execute the processor-executable instructions to perform functions described herein. The storage devices may be implemented as computer-readable storage media (i.e., tangible, non-transitory computer-readable media) encoded with the processor-executable instructions; examples of suitable computer-readable storage media are discussed below.

Each of the processing components of motor function characterization system 114, including analyzers 116, 118 may be implemented in software, hardware, or a combination of software and hardware. Components implemented in software may comprise sets of processor-executable instructions that may be executed by the one or more processors of motor function characterization system 114 to perform the functionality described herein. Each of user input analyzer 116 and motor function analyzer 118 may be implemented as a separate component of motor function characterization system 114 (e.g., implemented by hardware and/or software code that is independent and performs dedicated functions of the component), or any combination of these components may be integrated into a single component or a set of distributed components (e.g., hardware and/or software code that performs two or more of the functions described herein may be integrated, the performance of shared code may be distributed among two or more hardware modules, etc.). In addition, any one of user input analyzer 116 and motor function analyzer 118 may be implemented as a set of multiple software and/or hardware components.

Although the exemplary embodiment of FIG. 1 depicts user input analyzer 116 and motor function analyzer 118 implemented together on motor function characterization system 114, this is only an example; in other examples, any or all of the components may be implemented on one or more separate machines, or parts of any or all of the components may be implemented across multiple machines in a distributed fashion and/or in various combinations. It should be understood that any such component depicted in FIG. 1 is not limited to any particular software and/or hardware implementation and/or configuration.

For ease of explanation, examples set forth below will be described with reference to components of the system 100 of FIG. 1. It should be appreciated, however, that embodiments are not limited to operating in the exemplary environment of FIG. 1 or in similar environments.

As discussed above, in some embodiments an evaluation of motor function may include an analysis of time information associated with keystroke events, such as a sequence of events received by a user input analyzer 116. In some embodiments, the time information may be produced from analysis of timestamp information associated with each keystroke event indicating a time when a user pressed a key and when output from user interface 104 was received by control software 108 and/or passed to user input analyzer 116. In some embodiments, user input analyzer 116 may not receive keystroke events associated with timestamp information and may itself determine time information to associate with keystroke events. For example, in some embodiments the user input analyzer 116 may receive keystroke events in real time as the events are generated in response to user input to the interface 104 and may associate a time with each keystroke event as the event is received by the user input analyzer 116. Timestamp information may be in any suitable format, including an absolute time such as time of day or a relative time to a certain point in time such as when the user began providing the user input.

From an analysis of timestamp information for keystroke events of the sequence, user input analyzer 116 may identify time intervals for certain keystroke events and/or between certain keystroke events. The time intervals may identify lengths of time for the certain keystroke events or between keystroke events. The time intervals may correspond to keystroke dynamics time variables such as hold time, flight time, press latency, and release latency. Other time intervals may identify other aspects of timing of keystroke events. In some embodiments, time intervals may correspond to a user pressing a first key followed by a second key before releasing the first key. The time intervals may identify lengths of time where the user is pressing two keys at once.

Figure 2:
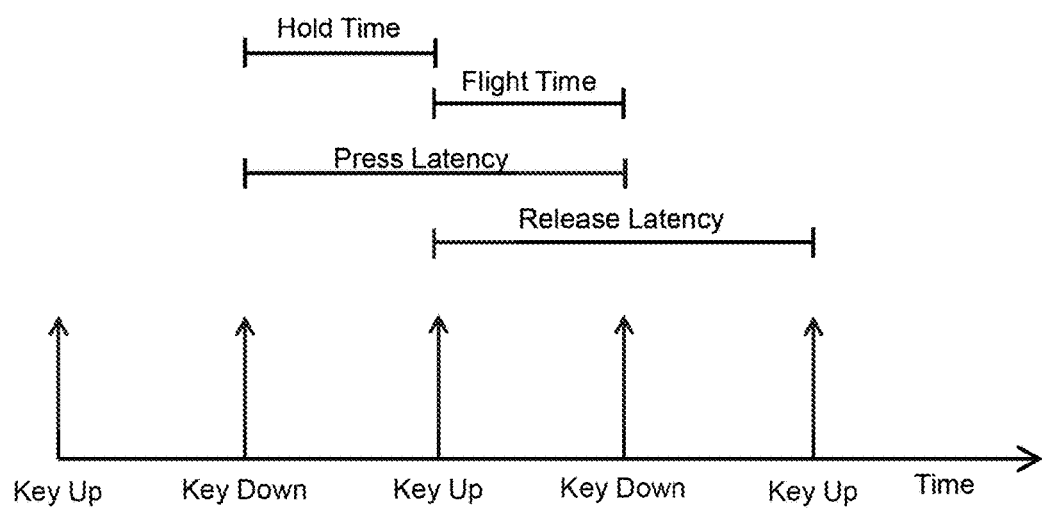
FIG. 2 is a schematic illustrating different keystroke dynamic variables.

FIG. 2 illustrates a schematic of possible time variables that may be identified by user input analyzer 116. For example, user input from a user pressing keys on a keyboard or regions on a touch screen may provide a sequence of key up and key down events over time, as shown in FIG. 2. Time intervals between key up and key down events may be determined by user input analyzer 116. In some embodiments, a keystroke time interval may be identified for a keystroke event, or between two keystroke events that relate to a user depressing one key, such as a key down event and a subsequent key up event. Such a keystroke time interval may be referred to as "hold time" and may refer to the time between when the user depresses that one key and when the user releases that one key. Additionally or alternatively, a keystroke time interval may be identified between subsequent keystroke events that relate to a user switching between keys, which may be referred to as "flight time." Such a keystroke time interval may refer to a time between a user releasing one key and depressing the next, and as such may correspond to a time between a key up event and a subsequent key down event. In some embodiments, a keystroke time interval may be identified between keystroke events related to a user pressing a key followed by pressing a subsequent key. Such a time interval between a key down event and a key up event may be referred to as "press latency," while a time interval between a key up event and a key down event may be referred to as "release latency."

Other suitable time intervals between keystroke events than the time intervals discussed in FIG. 2 may be analyzed by user input analyzer 116. A sequence of keystroke events may include adjacent "key up" events and/or adjacent "key down" events. In some embodiments, a time interval may correspond to a length of time between a "key up" event and another "key up" event that immediately follows the first "key up" event in the sequence, and/or two "key down" events that are similarly adjacent in the sequence. As an example, a user may press a key prior to releasing a previous key, creating a sequence of keystroke events with two "key down" events, with one immediately following the other in the sequence. This may correspond, for example, to the user pressing two keys at once, such as when a user inadvertently strikes two keys or when a user presses and holds one key while pressing another key, such as when the user is pressing a combination of keys, or when the user means to strike two keys in succession but strikes the next key before releasing the first key.

Event time intervals identified by user input analyzer 116 may be provided to motor function analyzer 118 to characterize motor function of the user providing the user input. In some embodiments, the motor function analyzer 118 may determine distributions of keystroke event intervals identified by user input analyzer 116. A distribution may be any suitable representation of the variation of keystroke event intervals over a time period. In some embodiments, a distribution may be a histogram and include counts of keystroke event intervals within certain ranges over a time period. A histogram may be constructed by identifying a range of values for keystroke event intervals over a time period and dividing the range into a series of small intervals, which may be referred to as "bins." To generate the histogram, the analyzer 118 may allocate each occurrence of a keystroke event interval over the time period to one of the bins, which is the bin having an interval that matches the interval of that keystroke event. The analyzer 118 may then determine a number of occurrences for each bin. In some embodiments, a distribution may be continuous, such as a probability distribution function, rather than a discrete histogram. The probability distribution function may be identified by estimating a function based on a resulting histogram. Though, it should be appreciated that these are merely examples and other types of statistical distributions and functions for characterizing time intervals may be used according to techniques described herein.

Figure 3A:
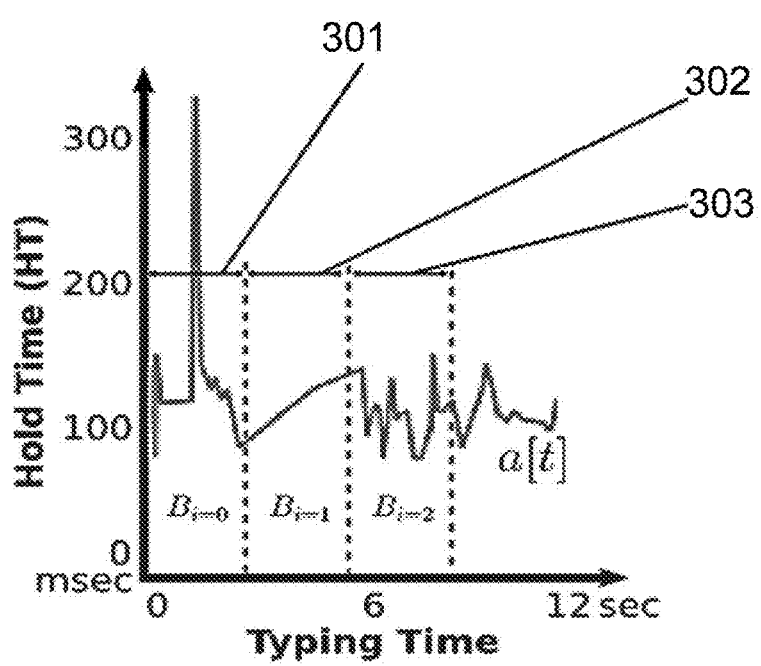
FIG. 3A is a graph illustrating an exemplary plot of hold time values as a function of time.
Figure 3B:
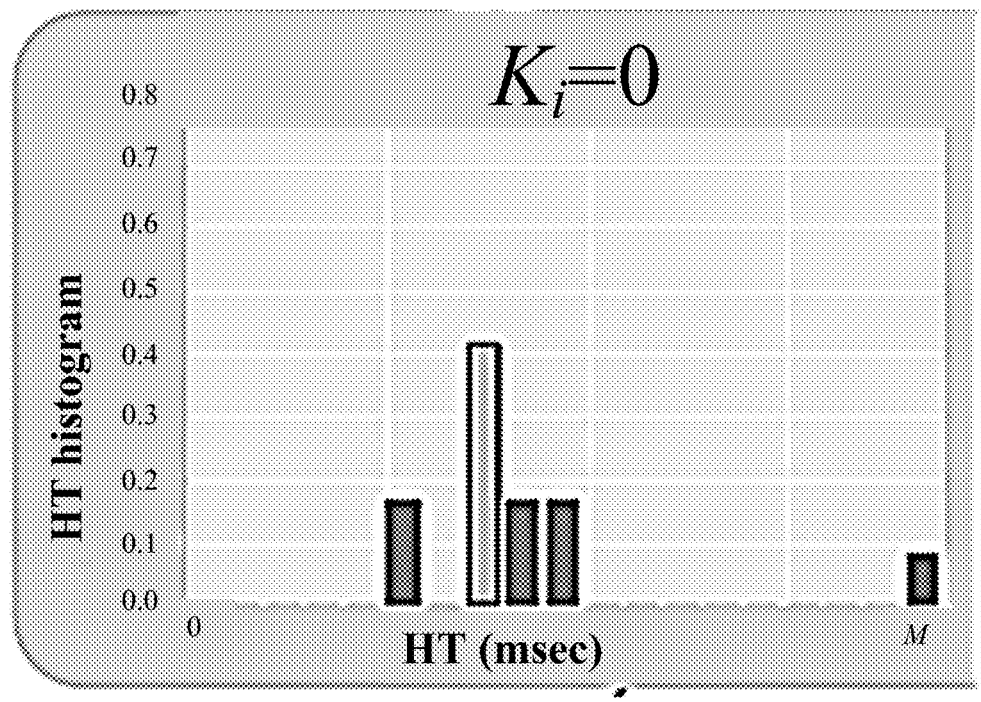
FIG. 3B-D are graphs of exemplary distributions of hold time values.
Figure 3C:
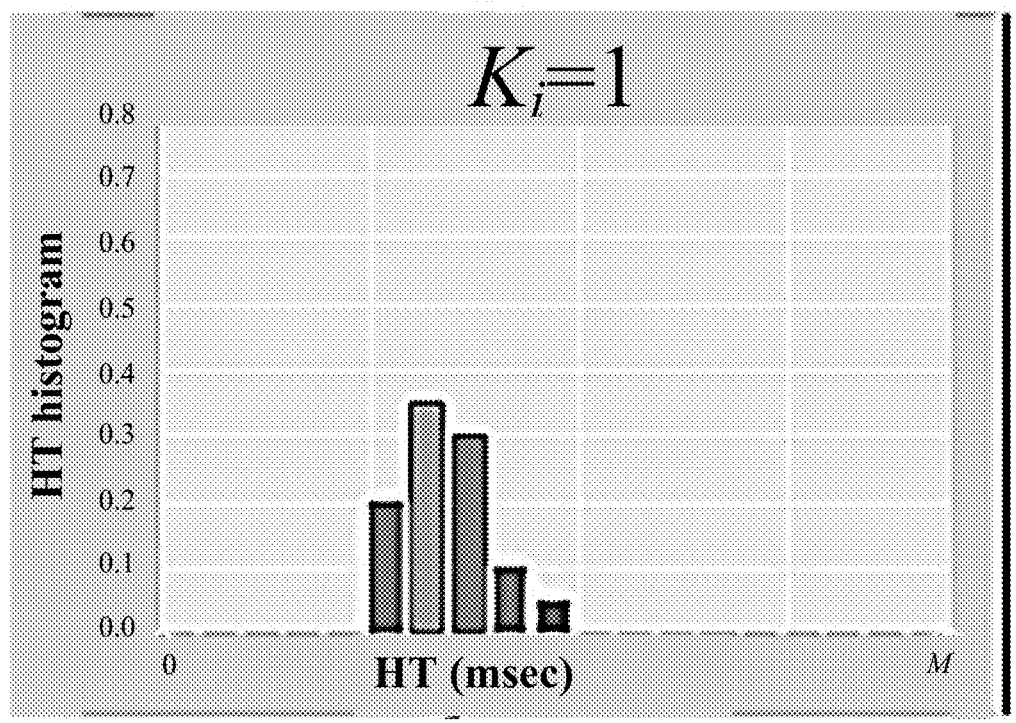
Figure 3D:
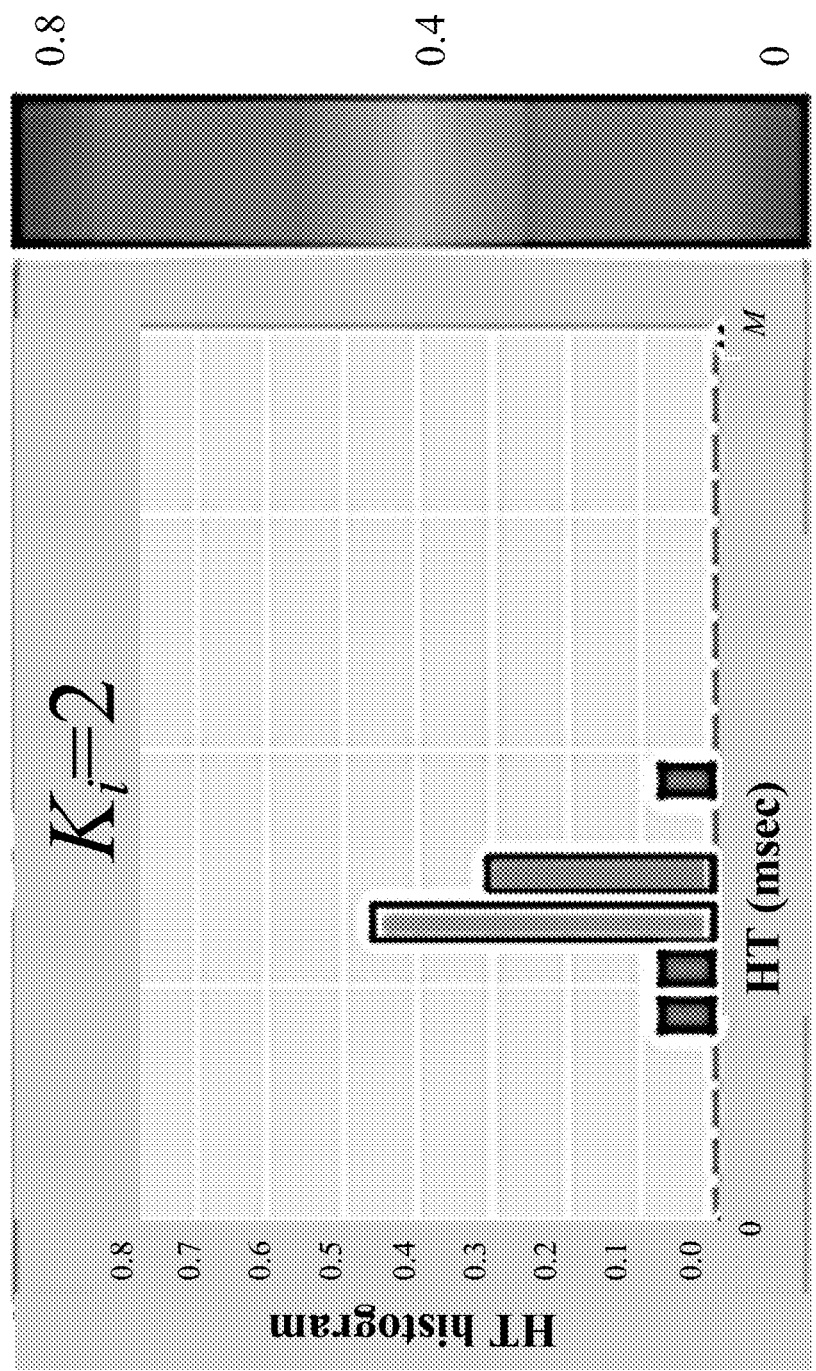
Figure 3E:
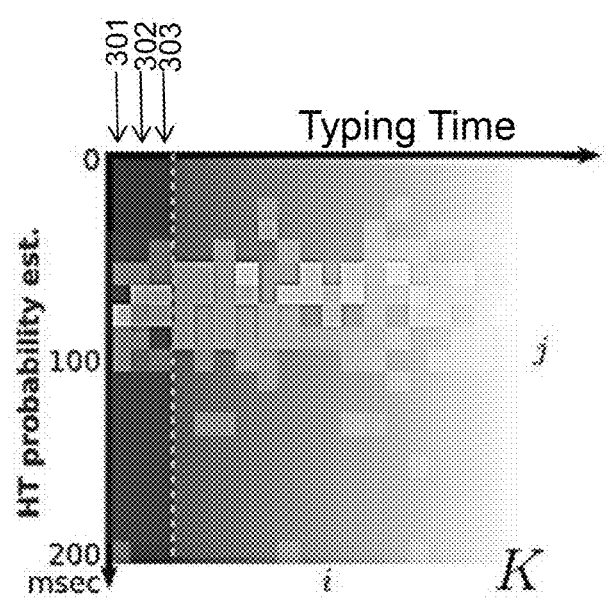
FIG. 3E is a visual representation of an exemplary plurality of distributions.

An exemplary analysis of keystroke events to determine a plurality of distributions of hold time by motor function analyzer 118 is illustrated in FIGS. 3A-3E. FIG. 3A illustrates variation in hold time values as a person is typing. Individual hold time values may be determined by identifying intervals of time when a key is pressed. Distributions of hold time may be determined for time periods 301, 302, and 303. FIGS. 3B-D illustrate exemplary distributions of hold time values as histograms for time periods 301, 302, and 303, respectively. In this example, FIG. 3B illustrates a histogram corresponding to a distribution of hold times within time period 301 of FIG. 3A, and the high hold time value is shown as a count on the right of histogram in FIG. 3B. Similarly the histogram illustrated in FIG. 3C corresponds to a distribution of hold times within time period 302 of FIG. 3A, and histogram illustrated in FIG. 3D corresponds to a distribution of hold times within time period 303. As distributions of hold times over subsequent time periods are determined, multiple distributions may be determined by motor function input analyzer 118. These distributions may be represented in a series, such as illustrated in FIG. 3E, where each column corresponds to values of histogram determined for one time period. In FIG. 3E, the column on the left corresponds to the histogram values from time period 301, the next column corresponds to the histogram values from time period 302, and the subsequent column corresponds to the histogram values from time period 303. In this manner, a set of distributions may be obtained over a time duration while a user is providing user input. The values of the set of distributions may be represented as a matrix where either the rows or columns indicated different distributions. As an example, a matrix, K, having j rows and i columns may include the values illustrated in FIG. 3E, where each column corresponds to a different distribution (e.g., i=0 corresponds to distribution from time period 301, i=2 corresponds to distribution from time period 302, and i=3 corresponds to distribution from time period 303).

Analysis of hold time values is provided as an example in FIGS. 3A-3E. It should be recognized that other types of time variables, such as flight time, press latency, and release latency, may be analyzed using these techniques to determine a plurality of distributions. Additionally or alternatively, other types of distributions may be determined for certain time periods, such as probability distributions, to determine a plurality of distributions.

Some embodiments relate to analyzing a plurality of distributions, such as illustrated in FIG. 3E, to provide an indication of a user's motor function. The inventors have recognized that variation among a plurality of distributions may provide an indication of a person's motor function. Variation among a plurality of distributions may include variation in an average value for each distribution of the plurality of distributions. Variation among a plurality of distributions may also include variation in distribution spread of the plurality of distributions. By distributions of a plurality, or by comparing a plurality of distributions with another plurality of distributions, information related to a condition or status of a person's motor function may be identified. When the distributions that are analyzed are spread over a time period, such as over a day, over a week, over a month, or over a year, or other time period, a comparison may provide an indication of changes in the person's condition that correspond to progression of a disorder and/or effectiveness of a treatment. Additionally or alternatively, a person's condition may be assessed by comparing a set of distributions based on user input provided by the person to a different set of distributions based on user input provided by another individual.

Figure 4:
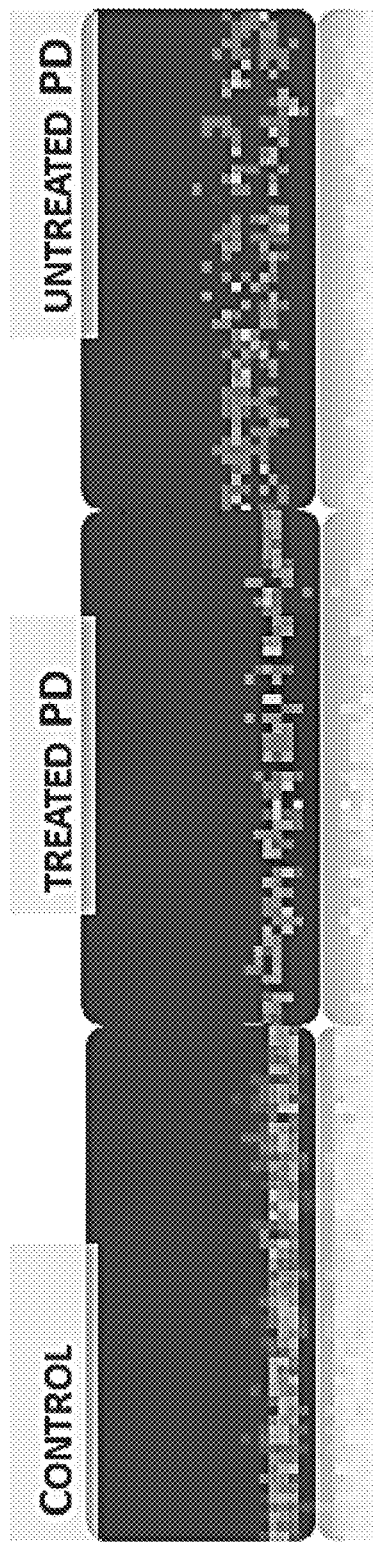
FIG. 4 are visual representations of exemplary pluralities of distributions that include treated and untreated individuals with Parkinson's disease and a control individual.

FIG. 4 illustrates different exemplary sets of distributions for a control individual having little or no motor function impairment ("Control"), a treated individual diagnosed with Parkinson's disease ("Treated PD"), and an untreated individual diagnosed with Parkinson's disease ("Untreated PD"). As shown in FIG. 4, the set of distributions for the control individual is characterized by limited variation in distribution spread and/or width among the distributions, while the sets of distributions for the treated PD individual and the untreated PD individual have broader variations in spread. Additionally, an average value may be identified for a set of distributions and provide a characterization of a person's motor function. As shown in FIG. 4, the control set of distributions has an average value lower than average values for treated and untreated PD sets of distributions. FIG. 4 also illustrates that limited variation of the distributions for the control individual may indicate a high level of stability of the user's motor function, while the broader variation of the distributions for the treated and untreated PD individuals may indicate a lower level of stability of the user's motor function.

FIG. 4 also illustrates that distributions of keystroke event intervals may provide an indication of effectiveness of treatment for a condition in improving motor function. A change in the variation among distributions (e.g., distribution spread or width) over time may provide an indication of a change in the user's motor function. As shown in FIG. 4, the distributions for an untreated individual has a broader spread or width of the distributions than for a person with Parkinson's disease undergoing treatment. By observing a decrease in the spread of the distributions over time during the course of treatment, and the treatment may be evaluated as reducing symptoms related to Parkinson's disease.

Figure 5:
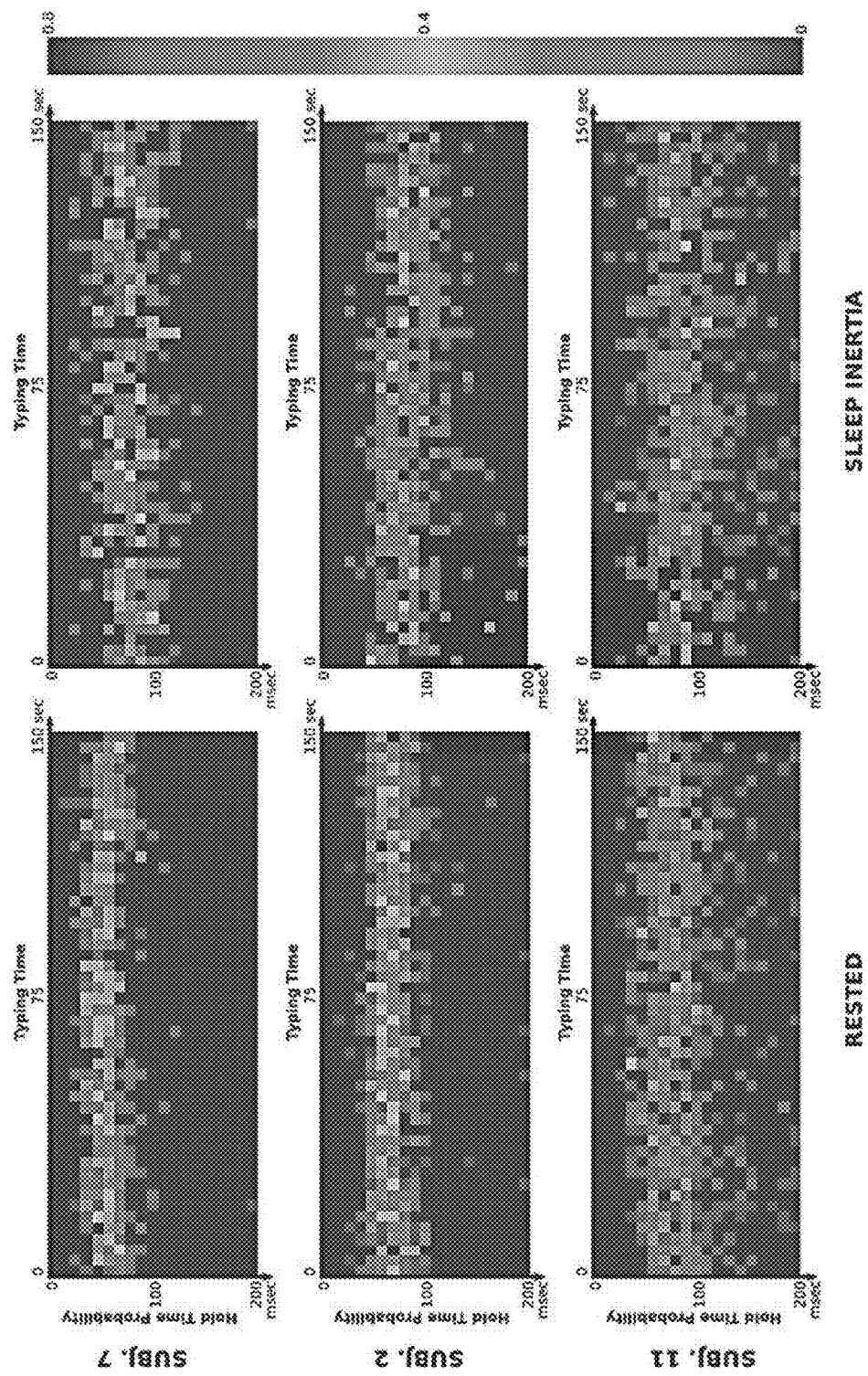
FIG. 5 are visual representations of exemplary pluralities of distributions for individuals in a rested state and a state of sleep inertia.

Further examples of sets of distributions acquired through the techniques discussed above are provided in FIG. 5 which illustrates sets of distributions for three subjects each in a rested state and a state of sleep inertia. Sleep inertia may be characterized as an impaired cognitive performance upon awakening. Individuals in a state of sleep inertia may have reduced motor impairment than when they are in a rested state. By having a user perform typing tasks over a duration of time, distributions of time intervals may be determined. In FIG. 5, distributions of hold times are determined when each subject is in a rested state and a state of sleep inertia. Variations among the distributions may provide an indication of the subject's motor function. As an example, subject 7 while in a rested state has a set of distributions with little variation in spread among the distributions in comparison to the set of distributions for subject 7 while in a state of sleep inertia. The motor function of subject 7 in a state of sleep inertia may be determined to be impaired based on the comparison. Similar comparisons may be performed for both subjects 2 and 11 to identify increased motor impairment when the subjects are in a state of sleep inertia.

As part of comparing one plurality of distributions to another plurality of distributions, one or more features for a plurality distributions may be identified to characterize the distributions. A feature may be one or more values calculated from a plurality of distributions and may provide an indication of a characteristic related to a user's motor function. Rather than visually comparing two sets of distributions, the one or more features may provide a quantitative metric to compare. Analysis of a plurality of distributions by motor function analyzer 118 may include identifying one or more features. A feature may provide an indication of an average value of the distributions. For example, median values for each distribution and an average value of the median values for the plurality of distributions may be determined. Another feature may correspond to variation in a spread of the plurality of distributions. Another feature may relate to the similarity of distributions within a plurality of distributions.

In some embodiments, a feature may include one or more characteristics of at least a portion of the distributions. A characteristic may be a median value, an average value, a peak value, a spread of the distribution, or a width of a distribution. An average value of a characteristic across multiple distributions may be determined. The average value may provide an indication of stability of a user's motor function. As an example, high hold time values may correspond to impaired motor function. Additionally, a feature may provide an indication of a user's motor function even when there are only a few data points available over a time period for a distribution. In some embodiments, identification of a feature may include calculating a median value for a distribution of keystroke event intervals. Multiple median values may be calculated for each of a plurality of distributions. Identification of a feature may include calculating an average value by averaging the median values to obtain an average median value for the plurality of distributions. In some embodiments, a feature calculated from a plurality of distributions may be an average value of median hold time values. An average value of median hold times may provide an indication of a user's motor function since motor impairment tends to correspond to increased values for hold time. Any suitable type of characteristic of the distributions may be averaged to provide an indication of a user's motor function. In some embodiments, a feature may be calculated by averaging peak values of multiple distributions of keystroke event intervals.

As an example, an average value, $K^P$, of a median values for a plurality of distributions, K, having z columns may be calculated based on the following mathematical expression where K is a matrix having i columns and j entries in each column:

$$K^P = \frac{\sum_{i=0}^{z} \mathrm{argmax} K_{j,i}}{z}$$

In some embodiments, a portion of distributions may be used to determine one or more features may be determined to reduce including distributions with an insufficient amount of information in the calculation. In some embodiments, a distribution may be selected for calculating one or more features based on identifying a number of non-zero elements for the distribution and comparing the number of non-zero elements to a threshold number. If the number of non-zero elements of a distribution is greater than the threshold number then, the distribution may be included as part of calculation of a feature for a set of distributions.

Some embodiments relate to calculating a feature indicating a degree of stability among a plurality of distributions. Stability among a plurality of distributions may provide an indication of a user's motor function where a higher instability may indicate an impaired motor function. Identification of a feature that provides an indication of stability across distributions may include comparing at least a first distribution to at least a second distribution to obtain a degree of similarity. In some embodiments, a feature may be identified by comparing each distribution of a plurality of distributions to each other to obtain a degree of similarity among the plurality of distributions. Any suitable type of analysis to compare one distribution to another may be used including statistical correlation techniques (e.g., pairwise correlation), distance metrics, similarity metrics, and/or other comparisons techniques.

A feature indicating a degree of stability for a plurality of distributions may be determined by calculating a self-similarity matrix for the plurality of distributions. In some embodiments, a portion of the plurality of distributions may be used in calculating the self-similarity matrix. Any suitable distance metric may be used in calculating a self-similarity matrix for a plurality of distributions. In some embodiments, a distance metric may calculate a variation between two distributions by identifying a value representing differences between the two distributions. As an example, a distance metric used for calculating a difference between two distributions may be $d(x, y) = \|x - y\|$, where $x$ and $y$ are vectors representing the two distributions. A distance metric for each pair combination of distributions may be calculated to determine a self-similarity matrix. An example self-similarity matrix, $S$, is indicated by the following mathematical expression, where $K_{t=n}$ is the distribution of the plurality of distributions at time period $n$ and a distance metric is calculated for each entry in the self-similarity matrix:

$$S = \begin{pmatrix} d(K_{t=0}, K_{t=0}) & d(K_{t=0}, K_{t=1}) & \ldots & d(K_{t=0}, K_{t=n}) \\ \vdots & \vdots & \ddots & \vdots \\ d(K_{t=n}, K_{t=0}) & d(K_{t=n}, K_{t=1}) & \ldots & d(K_{t=n}, K_{t=n}) \end{pmatrix}$$

Figure 6:
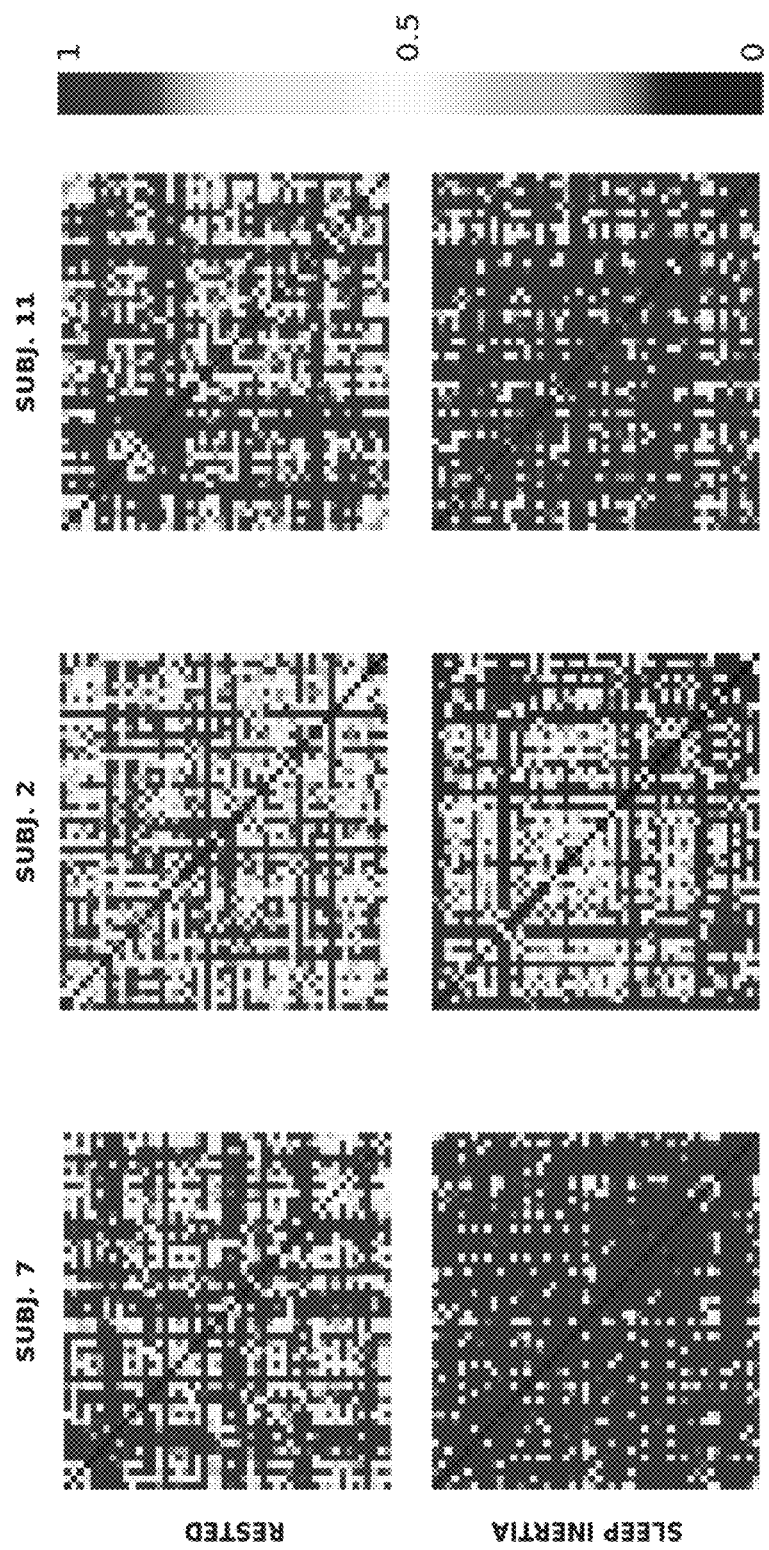
FIG. 6 are visual representations of exemplary self-similarity matrices for different pluralities of distributions.

The degree of variation within a self-similarity matrix may indicate a degree of stability for the plurality of distributions for a user. More variation within a self-similarity matrix may be indicated by higher distance metrics. Higher distance metric values may also indicate impairment of the user's motor function. In some embodiments, the self-similarity matrix, $S$, is normalized such that the range of values for the self-similarity matrix cover a range of scalar values (e.g., from 0 to 1). FIG. 6 illustrates visual representations of different self-similarity matrices corresponding to sets of distributions based on user input from three different subjects while each in a rested state and a state of sleep inertia. Variations in greyscale indicate a value of each distance metric from 0 to 1, where 0 indicates that there is no variation.

Some embodiments relate to a feature calculated by summing one or more distance metrics determined for similarity matrix, such as the self-similarity matrix discussed above. Such a feature may provide an overall indication of a degree of similarity for a plurality of distributions corresponding to variation among the plurality of distributions. Summed distance metric values for different sets of distributions may be compared to provide an indication of change in a user's motor function. For example, a higher summed distance metrics value may provide an indication of impaired user motor function.

It should be appreciated that other types of features calculated from a plurality of distributions may be used to provide an indication of a user's motor function, and aspects of the present application are not limited to the exemplary features described herein.

Some embodiments relate to determining and comparing one plurality of distributions to another plurality of distributions to assess an individual's motor function and/or monitor an individual's motor function. In some embodiments, one or more features for a plurality of distribution may be compared to one or more features of another plurality of distributions. The two pluralities of distributions may be from the same individual or different individuals. One plurality of distributions may be provided as a control or reference used to compare the other plurality of distributions. In some instances, the control or reference plurality of distributions may be from an earlier point in time than a current plurality of distributions. By comparing one plurality of distributions to another plurality of distributions, changes to one or more features may be identified which may indicate a degree of motor function capabilities of an individual. In this manner, a plurality of distributions based on user input for a time duration may serve as a biosignature for the user's motor function for the time duration.

In some embodiments, one or more features for a plurality of distributions may be compared to one or more features for another plurality of distributions. A difference between one plurality of distributions and another plurality of distributions may be identified based on comparing the one or more features for the two different pluralities of distributions. In some embodiments, a feature related to distribution spread may be compared between a first plurality of distributions and a second plurality of distributions, and a change in the user's motor function may be identified based on a result of the comparison. In some embodiments, a score indicative of a user's motor function may be calculated based on comparing one or more features for the two different pluralities of distributions.

Some embodiments relate to representing one or more features for a plurality of distributions as a vector by including values for the one or more features as components of the vector. Comparison between a first plurality of distributions and a second plurality of distributions may include calculating a first vector for the first plurality of distributions and a second vector for the second plurality of distributions. A difference between the first vector and the second vector may provide an indication of a change in the one or more features included as components of the first vector and the second vector.

In some embodiments, information on measurement data from one or more sensors such as movement, location, orientation, voice and/or pressure data may be analyzed, and a feature related to the analyzed data may provide an indication a user's motor function. A feature related to sensor measurements may be tracked over time and may be combined with one or more features related to a plurality of distributions as part of assessing a user's motor function. In some embodiments, a feature related to sensor measurements may be included as a component in a feature vector.

In some embodiments, a feature vector for a plurality of distributions may include features relating to an average value of median keystroke event intervals for the plurality of distributions. Determining the average value may include averaging a plurality of median values. Each median value identifying a median keystroke event interval for a distribution in a plurality of distributions. The feature vector may also include a degree of similarity for the plurality of distributions, such as a value calculated by summing distance metrics from a self-similarity matrix as discussed above. A first vector having values corresponding to at least these two features of a first plurality of distributions may be compared to a second vector having values corresponding to at least these two features of a second plurality of distributions. A difference between the first vector and the second vector may be calculated and may indicate a change in a user's motor function. The first vector and the second vector may be based on user input from the same user at different times, providing an indication of a change in the user's motor function over time.

Figure 7F:
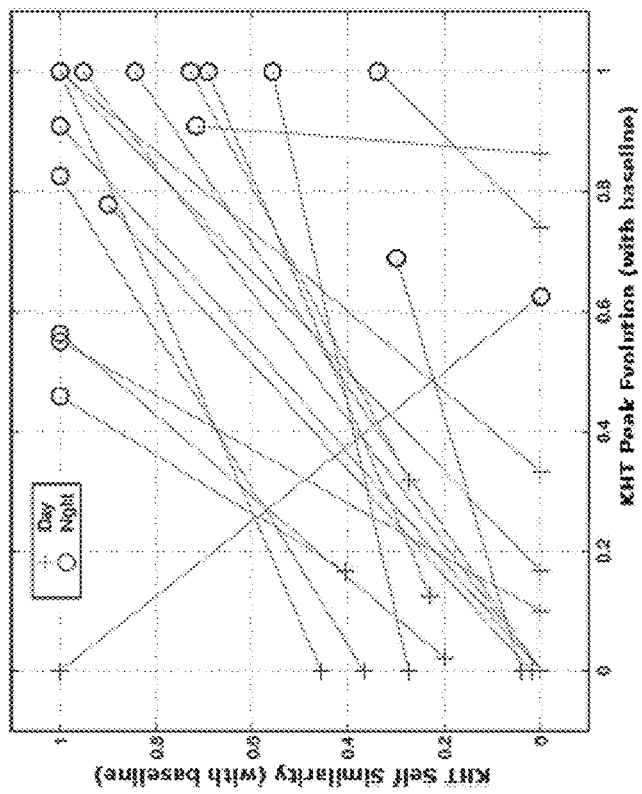
FIGS. 7E and 7F are plots illustrating variation in two features for different pluralities of distributions corresponding to data obtained from individuals during day and night in a sleep inertia study.
Figure 7E:
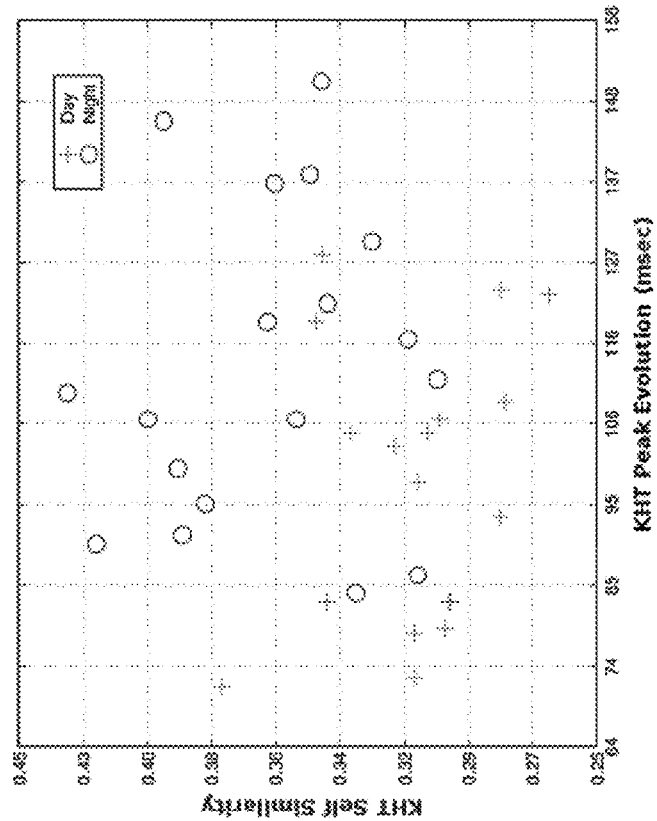

An illustrative example of calculating feature vectors is shown with respect to FIG. 7 which plots circular histograms indicating variation in average value of medians (as the x-component) and summed value of distance metrics from a self-similarity matrix (as the y-component). FIGS. 7A-D illustrate experimental results for quantifying fatigue via a sleep inertia protocol. Individuals were awakened during the night to induce sleep inertia and tested four times twice during the day and twice during the night. Each test consisted of 15 minutes of typing different text on different computers. FIGS. 7A and 7B illustrate a difference between a feature vector based on user input data when an individual is in a rested state and a second feature vector based on user input data when the individual is in a state of sleep inertia. An indication of the difference between the two vectors is shown by line 700 in FIG. 7A and line 702 in FIG. 7B. FIGS. 7C and 7D illustrate little to no significant difference when comparing two feature vectors when the individual is in a similar state for both feature vectors, such as during rested states as in FIG. 7C and during sleep inertia states as in FIG. 7D. FIGS. 7E and 7F plot average value of medians (along the x-axis) and summed value of distance metrics from a self-similarity matrix (along the y-axis) for different sets of distributions from individuals during the day (+) and night (O). FIGS. 7E and 7F illustrate an alternative representation of the data illustrated in FIGS. 7A-D. FIG. 7E illustrates higher values for both features (i.e. average value of medians and summed value of distance metrics) during the night than during the day indicating that these features are representative of impaired motor function due to sleep inertia. FIG. 7F illustrates data similar to that shown in FIG. 7E, but the data is normalized to a baseline level for each individual. The lines in FIG. 7E identify changes between day and night, illustrating that both these features increase at night when individuals are woken to perform typing tasks.

Figure 8B:
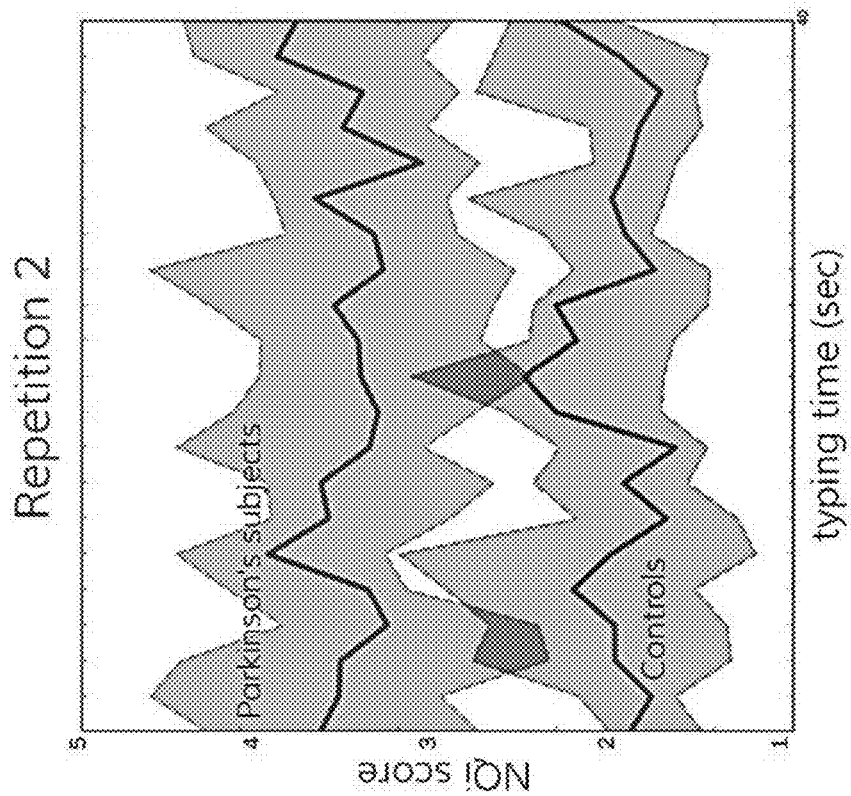
FIGS. 8A and 8B illustrate representative profiles for scores determined by a machine learning classier for individuals with Parkinson's disease and control individuals.
Figure 8A:
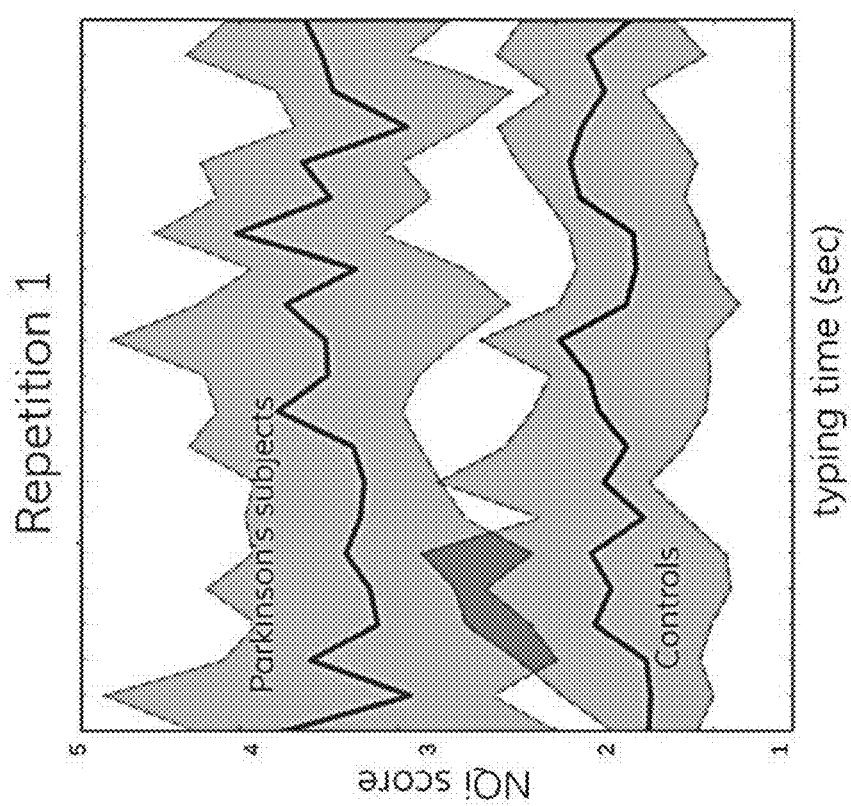

In some embodiments a score for a plurality of distributions may be determined by analyzing one or more quantiles for a plurality of distributions. A first quantile and a second quantile may be determined for a distribution of the plurality of distributions. Keystroke event intervals in the distributions may be identified as outliers based on the first quantile. A number of outliers in the distribution may be calculated based on one or more identified outliers in the distribution. The number of outlier may be normalized by a number of key presses for the distribution. A difference between the first quantile and the second quantile, a standard deviation of the outliers, and a value based on part of a covariance of the plurality of distributions may be calculated. A feature vector may be determined based on the number of outliers, the difference between the first and second quantiles, the standard deviation of the outliers, and the value based on part of the covariance. In some embodiments, a machine learning classifier or regressor (e.g., Support Vector Machine, Decision Trees, Neural Network) may output a score by learning examples of feature vectors representative of different levels of motor impairment and/or different conditions that may exist in a person (e.g., neurological disorders or impairments). The output score may be obtained over time by calculating the same feature vector and applying the classifier or regressor previously trained. The output score may be used to monitor changes in a user's motor function. FIGS. 8A and 8B illustrate representative profiles for scores determined by the machine learning classier based on individuals with Parkinson's disease and control individuals.

The invention is useful in some aspects for detecting changes in a person's "motor function" in order to collect information regarding a variety of conditions that may exist in the person, including neurological disorders the person may be suffering from or other neurological impairments such as brain injury (i.e. concussions), motor illnesses such as osteoarthritis, psychiatric conditions such as personality disorders, depression, anxiety, psychosis, developmental disorders, transient conditions such as intoxication, fatigue, stress and dehydration. This type of information can be useful, for instance, alone or in combination with other detection/diagnostic methods to aid in diagnosing a conditions, identifying early stages of disease, detecting changes in a condition influenced by environmental factors such as medicine or therapy, detecting temporary impairments associated with alcohol or drugs associated with psychomotor symptoms or fatigue, detecting early warnings of stroke or other debilitating diseases, where early intervention is critical.

Detection of neurodegenerative disease is an important utility of the methods and devices of the invention. Neurodegenerative diseases encompass a variety of disorders that involve progressive loss of structure and/or function of neurons in affected regions of the nervous system, often accompanied by neuronal loss. Many of the neurodegenerative diseases that affect the brain can lead to dementia, a devastating condition in which the loss of cognitive abilities detrimentally affects daily living and social functioning.

Neurodegenerative diseases include but are not limited to Parkinson's Disease, Parkinsonism, forms of Dementia such as Alzheimer's Disease or Mild Cognitive impairment, Multiple sclerosis, Amyotrophic lateral sclerosis. Neurological disease include, but are not limited to, Schizophrenia, Bipolar disorder, Autism, Epilepsy and Depression. Neurological impairments include brain injury (e.g. concussions), motor illnesses such as osteoarthritis, psychiatric conditions such as personality disorders, anxiety, psychosis, developmental disorders, and transient conditions such as intoxication, fatigue, stress and dehydration.

The methods and devices described herein can be used to detect properties associated with these disorders, often in earlier stages than the diseases can be detected by other methods. If a disease is detected using the methods of the invention, the presence of the disease or other properties such as the subtype or stage or degree of the disease can be further assessed by alternative methods known in the art. Alternatively if a disease is detected using other methodology it may be verified or further characterized using the methods of the invention. A number of properties associated with these diseases are well known in the art and may be used for further characterization.

Parkinson's disease is pathologically characterized by the presence of cytoplasmic Lewy bodies, major components of which are filaments composed of the neuronal protein alpha-synuclein, in neurons within the brain. Alpha-synuclein aggregates have been associated with several neurological diseases. A number of dominant point mutations in alpha-synuclein that cause familial early onset Parkinson's disease have been described. Duplication and triplication of the alpha-synuclein gene, leading to overproduction of alpha-synuclein, have also been linked to familial early-onset Parkinson's disease. In vitro studies have demonstrated that recombinant alpha-synuclein can form Lewy body-like fibrils that recapitulate the ultrastructural features of alpha-synuclein aggregates isolated from patients with Parkinson's disease. Certain Parkinson's disease-linked alpha-synuclein mutations have been shown to accelerate the aggregation process. Parkinson's disease is clinically characterized by bradykinesia, rigidity, resting tremor, and postural rigidity, a constellation of symptoms commonly referred to as "parkinsonism". Patients frequently develop cognitive impairment and depression as the disease progresses. Most motor symptoms can be attributed to the degeneration of dopaminergic neurons within the substantia nigra pars compacta, a key regulatory nucleus of the basal ganglia circuitry. However, several other nondopaminergic neuronal populations may also degenerate, including various autonomic nuclei and the locus ceruleus as well as glutamatergic neurons throughout the cerebral cortex.

Alzheimer's disease is a neurodegenerative disorder characterized by neurofibrillary tangles and plaques containing an amyloid beta peptide. Patients with Alzheimer's disease exhibit progressive dementia, which may manifest with impairment in memory and cognitive abilities. Proteolytic cleavage of the amyloid precursor protein (APP) results in the generation of an amyloid beta peptide ranging typically from 38 to 43 amino acids long. The amyloid beta 1-42 peptide is particularly prone to self-aggregation and is strongly linked to development of Alzheimer's disease.

The methods and devices described herein may also be used to assess the effectiveness of a therapeutic agent or putative therapeutic agent, by detecting changes in the disease state or progression. The methods and devices may also be used for evaluating or monitoring the state of the disease. The terms "assessing", "determining", "evaluating", "assaying" are used interchangeably herein to refer to any form of detection or measurement of a change, and include determining whether a change in degree of disease or condition, etc., is present or not. The result of an assessment may be expressed in qualitative and/or quantitative terms. Assessing may be relative or absolute.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. Currently there is no cure for ALS; nor is there a proven therapy that will prevent or reverse the course of the disorder.

Currently, Parkinson's disease is treated with several different compounds and combinations, the effectiveness on a particular patient of which could be further assessed using the methods of the invention. Levodopa (L-dopa), which is converted into dopamine in the brain, is often given to restore muscle control. Perindopril, an ACE inhibitor that crosses the blood-brain barrier, is used to improve patients' motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimickers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

Autism (also referred to as Autism Spectrum Disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of autism is unknown, it appears to include one or more genetic factors, as indicated by the fact that the concordance rate is higher in monozygotic twins than in dizygotic twins, and may also involve immune and environmental factors, such as diet, toxic chemicals and infections.

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process.

The invention is also useful for characterizing or detecting motor illnesses or musculoskeletal diseases. A "motor illness" or "musculoskeletal disease" as used herein refers to a disorder that affects the body's muscles, joints, tendons, ligaments and nerves. These diseases include but are not limited to Osteoarthritis, Back pain, Rheumatoid arthritis, Osteoporosis, Septic arthritis, gout, Fibromyalgia, and Systemic lupus erythematosus (SLE).

Osteoarthritis (OA) is a common disorder resulting in a reduction in bone mass, affecting over 150 million people worldwide, making it one of the most prevalent diseases in the world (WHO, 2009). OA attacks body joints, affecting productivity and quality of life, and is extremely disabling to the patient. Current therapies only provide short term pain and inflammation relief but afford no protection against the inevitable further degeneration of joint cartilage, the hallmark of end-stage OA. This results in complete joint dysfunction (including deterioration of bone and other soft tissues), leading to the patient's need for joint replacement. It is thus vital to further understand OA disease mechanisms and to develop effective therapeutics and drug-delivery systems for curing it. In addition to detecting OA in a patient, the methods of the invention may be used to evaluate the effectiveness of putative therapeutics.

Drugs and alcohol can impair motor function. This type of impairment can cause serious problems such as overdose, violence, accidents and motor vehicle crashes. The methods and devices of the invention can be used to detect unacceptable levels of motor impairment due to drug or alcohol ingestion.

Additionally, different people react differently to different therapeutic treatments. The methods and devices of the invention may be used to monitor an individual patients reaction to a particular therapeutic. Detecting, for instance changes in motor function.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

Figure 9:
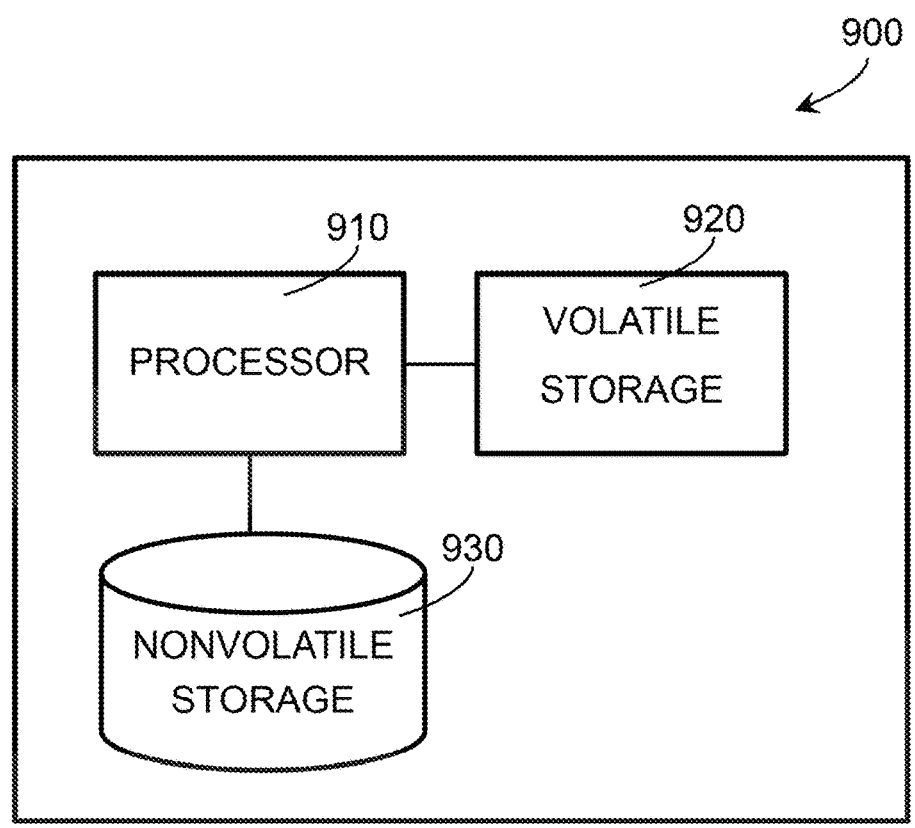
FIG. 9 is a block diagram of an exemplary computer system on which some embodiments may be implemented.

A motor function characterization system in accordance with the techniques described herein may take any suitable form, as embodiments are not limited in this respect. An illustrative implementation of a computer system 900 that may be used in connection with some embodiments is shown in FIG. 9. One or more computer systems such as computer system 900 may be used to implement any of the functionality described above. The computer system 900 may include one or more processors 910 and one or more computer-readable storage media (i.e., tangible, non-transitory computer-readable media), e.g., volatile storage 920 and one or more non-volatile storage media 930, which may be formed of any suitable data storage media. The processor 910 may control writing data to and reading data from the volatile storage 920 and the non-volatile storage device 930 in any suitable manner, as embodiments are not limited in this respect. To perform any of the functionality described herein, the processor 910 may execute one or more instructions stored in one or more computer-readable storage media (e.g., volatile storage 920 and/or non-volatile storage 930), which may serve as tangible, non-transitory computer-readable media storing instructions for execution by the processor 910.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation comprises at least one computer-readable storage medium (i.e., at least one tangible, non-transitory computer-readable medium), such as a computer memory (e.g., hard drive, flash memory, processor working memory, etc.), a floppy disk, an optical disk, a magnetic tape, or other tangible, non-transitory computer-readable medium, encoded with a computer program (i.e., a plurality of instructions), which, when executed on one or more processors, performs above-discussed functions. The computer-readable storage medium can be transportable such that the program stored thereon can be loaded onto any computer resource to implement techniques discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-techniques.

The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method for detecting motor impairment of a user by analyzing an input by the user to a user interface of at least one computing device, the method comprising:
   receiving a sequence of keystroke events indicating that the user pressed at least a portion of the user interface over a time duration;
   determining, by at least one processor, a biosignature indicative of the user's motor function at least in part by determining at least one distribution of time intervals corresponding to keystroke events that occur over at least some of the time duration; and
   detecting a degree of motor impairment in the user based on comparing the biosignature to a reference biosignature to determine variation between the biosignature and the reference biosignature, wherein the reference biosignature is determined at least in part by determining at least one second distribution of time intervals that correspond to keystroke events that occur over a second time duration and detecting the degree of motor impairment in the user further comprises:
      calculating at least one feature of the at least one distribution and the at least one second distribution by comparing the at least one distribution to the at least one second distribution to obtain a degree of similarity indicative of the variation among the at least one distribution and the at least one second distribution; and
      determining variation of the at least one feature between the at least one distribution and the at least one second distribution.

2. The method of claim 1, wherein the method further comprises:
   determining effectiveness of a treatment for the user based at least in part on the detected degree of motor impairment.

3. The method of claim 1, wherein the method further comprises:
   determining progression of a disease in the user based at least in part on the detected degree of motor impairment.

4. The method of claim 1, wherein the method further comprises identifying a presence of a neurological disease in the user based at least in part on the detected degree of motor impairment, wherein the presence of the neurological disease is identified prior to diagnosis of physical symptoms in the user.

5. The method of claim 1, wherein the method further comprises:
   comparing an amount of variation between the biosignature and the reference biosignature to a threshold value;
   in response to determining that the amount of variation is above the threshold value, generating a report identifying the user as having a high level of motor impairment; and
   in response to determining that the amount of variation is below the threshold value, generating a report identifying the user as having a low level of motor impairment.

6. The method of claim 1, wherein detecting the degree of motor impairment in the user further comprises analyzing the at least one distribution and the at least one second distribution of time intervals corresponding to keystroke events associated with the reference biosignature to determine a measure of variation in width between the at least one distribution and the at least one second distribution.

7. The method of claim 6, wherein the method further comprises:
   comparing the measure of variation in width to a threshold value representative of at least one healthy individual;
   in response to determining that the measure of variation in width is above the threshold value, determining the degree of motor impairment in the user as being a high level of motor impairment and generating a report identifying the user as having a high level of motor impairment; and
   in response to determining that the measure of variation in width is below the threshold value, determining the degree of motor impairment in the user as being a low level of motor impairment and generating a report identifying the user as having a low level of motor impairment.

8. The method of claim 1, wherein the method further comprises:
   receiving data measured by at least one sensor; and
   wherein detecting the degree of motor impairment in the user is further based on the data.

9. The method of claim 8, wherein the at least one sensor includes at least one from the group of an accelerometer, a gravity sensor, a gyroscope, a rotational vector sensor, an orientation sensor, a magnetometer, a pressure sensor, a thermometer, a barometer, a microphone, and a photometer.

10. The method of claim 1, wherein comparing the biosignature to the reference biosignature further comprises analyzing the at least one distribution of time intervals and the at least one second distribution of time intervals to determine variation of keystroke event intervals between the biosignature and the reference biosignature.

11. The method of claim 1, wherein the reference biosignature is associated with the user pressing at least a portion of the user interface over the second time duration.

12. The method of claim 1 wherein the reference biosignature is associated with a person different than the user pressing at least a portion of a user interface over the second time duration.

13. The method of claim 1, wherein:
   calculating the at least one feature comprises comparing each of the at least one distribution to each of the at least one second distribution to obtain a degree of similarity indicative of the variation among the at least one distribution and the at least one second distribution.

14. The method of claim 1, wherein:
   receiving the sequence of keystroke events comprises receiving a sequence of keystroke events input by the user while interacting with a plurality of applications executing on the at least one computing device.

15. The method of claim 1, wherein:
   receiving the sequence of keystroke events comprises detecting a plurality of keystroke events as a background task while the user is interacting with a device sensitive to touch.

16. An apparatus comprising:
a user interface; and
control circuitry configured to perform a method comprising:
   receiving a sequence of keystroke events indicating that the user pressed at least a portion of the user interface over a time duration;
   determining a biosignature indicative of the user's motor function at least in part by determining at least one distribution of time intervals corresponding to keystroke events that occur over at least some of the time duration; and
   detecting a degree of motor impairment in the user based on comparing the biosignature to a reference biosignature, wherein the reference biosignature is determined at least in part by determining at least one second distribution of time intervals that correspond to keystroke events that occur over a second time duration and detecting the degree of motor impairment in the user further comprises:
      calculating at least one feature of the at least one distribution and the at least one second distribution by comparing the at least one distribution to the at least one second distribution to obtain a degree of similarity indicative of the variation among the at least one distribution and the at least one second distribution; and
      determining variation of the at least one feature between the at least one distribution and the at least one second distribution.

17. An electronic device comprising:
a tactile interface for receiving a plurality of keystrokes;
a processor configured to receive user input from the tactile interface on the plurality of keystrokes; and
a storage medium storing processor executable instructions that when executed by the processor perform a method comprising:
   determining a biosignature indicative of the user's motor function at least in part by determining at least one distribution of time intervals corresponding to keystroke events that occur over at least some of the time duration; and
   detecting a degree of motor impairment in the user based on comparing the biosignature to a reference biosignature, wherein the reference biosignature is determined at least in part by determining at least one second distribution of time intervals that correspond to keystroke events that occur over a second time duration and detecting the degree of motor impairment in the user further comprises:
      calculating at least one feature of the at least one distribution and the at least one second distribution by comparing the at least one distribution to the at least one second distribution to obtain a degree of similarity indicative of the variation among the at least one distribution and the at least one second distribution; and determining variation of the at least one feature between the at least one distribution and the at least one second distribution.

18. A method for detecting motor impairment of a user by analyzing an input by the user to a user interface of at least one computing device, the method comprising:

receiving a sequence of keystroke events indicating that the user pressed at least a portion of the user interface over a time duration;

determining, by at least one processor, a biosignature indicative of the user's motor function at least in part by determining at least one distribution of time intervals corresponding to keystroke events that occur over at least some of the time duration; and detecting a degree of motor impairment in the user based on comparing the biosignature to a reference biosignature to determine variation between the biosignature and the reference biosignature, wherein the reference biosignature is determined at least in part by determining at least one second distribution of time intervals that correspond to keystroke events that occur over a second time duration and detecting the degree of motor impairment in the user further comprises:

calculating at least one feature of the at least one distribution and the at least one second distribution by comparing each of the at least one distribution to each of the at least one second distribution to obtain a degree of similarity indicative of the variation among the at least one distribution and the at least one second distribution; and determining variation of the at least one feature between the at least one distribution and the at least one second distribution.

19. An apparatus comprising:

a user interface; and control circuitry configured to perform a method comprising:

receiving a sequence of keystroke events indicating that the user pressed at least a portion of the user interface over a time duration;

determining a biosignature indicative of the user's motor function at least in part by determining at least one distribution of time intervals corresponding to keystroke events that occur over at least some of the time duration; and detecting a degree of motor impairment in the user based on comparing the biosignature to a reference biosignature, wherein the reference biosignature is determined at least in part by determining at least one second distribution of time intervals that correspond to keystroke events that occur over a second time duration and detecting the degree of motor impairment in the user further comprises:

calculating at least one feature of the at least one distribution and the at least one second distribution by comparing each of the at least one distribution to each of the at least one second distribution to obtain a degree of similarity indicative of the variation among the at least one distribution and the at least one second distribution; and determining variation of the at least one feature between the at least one distribution and the at least one second distribution.

* * * * *